United States Patent
Rhodes (12)

(10) Patent No.: US 6,383,498 B1
(45) Date of Patent: May 7, 2002

(54) COMPOSITIONS FOR VACCINES

(75) Inventor: John Richard Rhodes, Beckenham (GB)

(73) Assignee: Glaxo Wellcome Inc., Research Triangle Park, NC (US)

( * ) Notice: Subject to any disclaimer, the term of this patent is extended or adjusted under 35 U.S.C. 154(b) by 0 days.

(21) Appl. No.: 08/404,122

(22) Filed: Mar. 14, 1995

Related U.S. Application Data

(63) Continuation of application No. 07/969,215, filed as application No. PCT/GB91/01394 on Aug. 16, 1991.

(30) Foreign Application Priority Data

Aug. 17, 1990 (GB) .............................................. 9018061

(51) Int. Cl.$^7$ ........................ A61K 39/39; A61K 38/43; A61K 39/12; A61K 39/02; A61K 39/002
(52) U.S. Cl. ............................... 424/282.1; 424/204.1; 424/234.1; 424/269.1; 424/274.1; 424/94.2
(58) Field of Search ........................... 424/279.1, 282.1, 424/94.2, 204.1, 234.1, 269.1, 274.1; 514/885; 530/825

(56) References Cited

U.S. PATENT DOCUMENTS 4,510,129 A * 4/1985 Knop et al. ............... 424/159.1

FOREIGN PATENT DOCUMENTS

CH 630 807 A5 7/1982
DE 1569003 * 6/1980

OTHER PUBLICATIONS

Lipkowitz Et Al; J. Immunology 130 (6):2702–2707, 1983.*
Rhodes J., J. Immunology 143 (5) :1482–1489, 1989.*
Gao Et Al, J. Immunology 144 (8) : 2883–2890, 1990.*
Roitt Et Al, *Immunology* C. V. Mosby Company, Gower Medical Publishing (London), 1985 p 8.3.*
Ada G. L. Lancet 335 (8688) : 523–526, 1990.*
Sigma Chemical Company Catalog 1989 p 630.*
Roitt Et Al, *Immuology* C. V. Mosby Company Gover Medical Publishing (London) 1985 First Page of Glossary.*
Chemical Abstracrs, vol. 88, No. 21, May 22, 1978, Knop J et al, p. 420, abstract 150333s.
Stimulatory Effect of Vibrio Cholerae Neuraminidase on the Antibody Response to Various Antigens; Knop et al; Immunology 1978, 34 (2), pp. 178–187.
Chemical Abstraces, vol. 88, No. 25, Jun. 19, 1978, Sedlacek et al, Possible Immunological Action of Vibrio Cholerae Neuraminidase (VCN), p. 75.
Chemical Abstracts, vol. 97, No. 19, Nov., 1982, Sedlacek et al, "Tumor Immunotherapy Using the Adjuvant et al" p. 40, abstract 15606j.
The Journal of Immunology, vol. 115, No. 4, Oct. 1975, "The Requirement for Macrophage–Lymphocyte et al" Greineder et al, p. 932–938.
Dialog Information Services, File 154, Medline, accession No. 05924514, Wang et al, "Anti–Tumor Properties et al", Jun. 1986, 136 (12) pp. 4735–4739.
Methods in Enzymology, vol. 150, 1987, William E. Bowps: "Stimulation of Lymphocytes with Periodate et al" pp. 105–108.
Journal of Clinical Oncology, vol. 7, No. 12 (Dec.), 1989; A Phase II Clinical Trail of Adoptive Immunotherapy et al Wang et al, pp. 1885–1891.
Science, vol. 256, Jun. 12, 1992; Galactose Oxidation in the Design of Immunogenic Vaccines Zheng et al, pp. 1560–1563.
Novogrodsky et al, "Induction of Lymphocyte Tranformation by Sequential Treatment with Neuraminidase and Galactose Oxidase", Proc. Natl. Acad. Sci. USA 70(6):1824–1827 (1973).
Roffman et al, "The Extend of Oxidative Mitogenesis does not Correlate with the Degree of Aldehyde formation of the T Lymphocyte Membrane", The Journal of Immunology 137(1):40–44 (1986).
Phillips et al, "Characterization of Responding Cells in Oxidative Mitogen Stimulation II. Identification of an Ia–Bearing Adherent Accessory Cell", The Journal of Immunology 124(6):2700–2707 (1980).

* cited by examiner

*Primary Examiner*—James Housel
*Assistant Examiner*—Myron G. Hill
(74) *Attorney, Agent, or Firm*—Nixon & Vanderhye P.C.

(57) ABSTRACT

Neuraminidase and galactose oxidase together are a vaccine adjuvant.

10 Claims, 21 Drawing Sheets

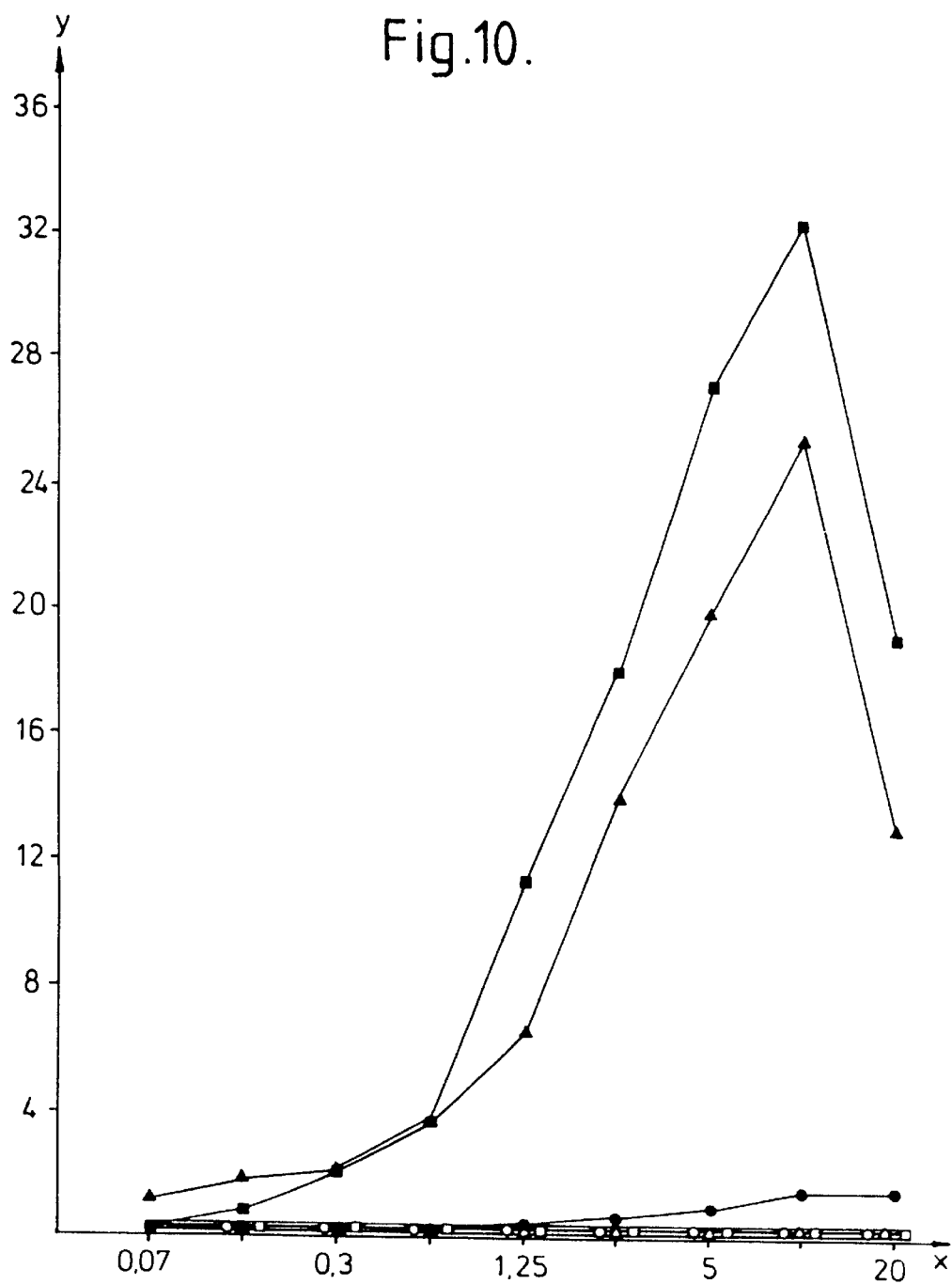

COMPOSITIONS FOR VACCINES

This is a continuation of application Ser. No. 07/969,215, filed Feb. 5, 1993, now abandoned, which is a National Stage application of PCT/GB91/01394, filed Aug. 16, 1991.

The present invention relates to vaccine adjuvants.

Vaccination has been chiefly responsible for the eradication of smallpox in man, and the control of numerous other infective agents in both animals and man. Traditionally vaccines have been whole organisms which are either attenuated, or killed. With the advent of recombinant DNA technology and increased understanding of immunology there has been much progress in producing sub-unit vaccines. Such vaccines are potentially free of problems associated with the traditional vaccines.

However, these new generation of vaccines are, on the whole, weakly immunogenic and thus require the presence of adjuvants (i.e. an agent that augments specific immune responses).

Materials having adjuvant activity are well known. Currently, however, Alum ($Al(OH)_3$), and similar aluminium gels are the only adjuvants licensed for human use. The adjuvant activity of alum was first discovered in 1926 by Glenny (Chemistry and Industry, Jun. 15, 1926; J. Path. Bacteriol, 34, 267). Other materials are also known to have adjuvant activity, and these include: Freund's complete adjuvant, a water-in-mineral-oil emulsion which contains killed, dried mycobacteria in the oil phase; Freund's incomplete adjuvant, a weaker formulation without the mycobacteria; saponin, a membrane active glucoside extracted from the tree Quillia saponaria; nonionic block copolymer surfactants, non metabolised synthetic molecules which tend to bind proteins to cell surfaces; ISCOMS, lipid micelles incorporating Quil A (saponin) which mimic, in physical terms, infectious particles; and muramyl dipeptide, a leukocyte stimulatory molecule that is one of the active components of killed mycobacteria.

With all of these agents toxicity, and unacceptable chronic reactions, depending on dose, are a feature which currently limit their use as potential alternatives to alum. Alum, on the other hand, will not stimulate cell-mediated immunity, and although having a broad spectrum of activity, is not effective in all potential vaccines, since in peptide vaccines, adsorption onto the alum may be poor due to the small size of the peptide. Occasionally, alum may induce the degradation of antigens by proteases with great efficiency. Thus it is apparent that there is a need for new adjuvants.

NAGO, a combination of neuraminidase and galactose oxidase, is known in the art to induce T lymphocyte proliferation by the induction of aldehydes on cell membranes, (J. Immunol, vol 115(4), p932–8).

The present inventors have now discovered that a combination of neuraminidase and galactose oxidase (NAGO) possesses potent adjuvant properties. NAGO has been found to be a non-reactogenic adjuvant of unprecedented potency in the induction of T-cell responses. In particular it was as effective or better than Freund complete adjuvant in the induction of cytotoxic T-cells induced with peptide but recognizing cells infected with live virus. It was also more effective than Freund complete adjuvant in priming T-cells to the envelope glycoprotein gp120 of human immunodeficiency virus. Strong adjuvant effects were exemplified with peptide and protein and polysaccharide antigens of bacterial, viral and protozoal origin. Local reactions produced by NAGO were very mild and were no different to, or less than, those induced by alhydrogel, the only adjuvant licensed for human use.

Accordingly the present invention provides a vaccine formulation comprising an antigenic component and, as an adjuvant component, neuraminidase and galactose oxidase. The invention also provides the use, as a vaccine adjuvant, of neuraminidase and galactose oxidase. A vaccine may therefore be prepared by formulating the antigenic component with, as adjuvant, neuraminidase and galactose oxidase.

It will of course be appreciated that galactose oxidase and neuraminidase may be obtained from any suitable source but preferably, galactose oxidase is isolated from *Dactilylium dendroides*. The galactose oxidase from *Dactilylium dendroides* (EC 1.1.3.9) may have an activity of between 200–900 units (or u) per mg protein. Neuraminidase is preferably isolated from *Vibrio cholerae* or *Clostridium perfringens*. The *Vibrio* material (EC 3.2.1.18) preferably has an activity of 25u per µg of protein (defined by the commercial source, BDH, Poole, Dorset, GB). When isolated from *Clostridium*, the enzyme preferably has an activity of 150–400 units per mg protein, although a partially purified material of 1 unit per mg solid has also shown to be effective. Both enzymes are commercially available from, for example, Sigma Chemical Company, Poole, Dorset, GB.

Preferably the ratio of neuraminidase to galactose oxidase in terms of units of activity is from 1:2 to 1:10 but optimally is about 1:5. The amount of NA per 100 µl of material for injection may be from 0.05 to 12u, preferably from 0.2 to 1.2u. The amount of GO per 100 µl of material for injection may be from 0.1 to 25u, preferably from 2 to 8u. The optimal amount is 1 u NA and 5u GO per 100 µl of material for injection.

Antigens which may be particularly useful in a vaccine formulation include peptide, protein and carbohydrate antigens. The antigens may be bacterial, fungal, protozoal or viral antigens. The antigens may be subunit antigens from influenza (J. Immunol. 143 p3007, 1989), subunit antigens from human immunodeficiency virus (Lancet 335 p1081, 1990), such as gp 120, and subunit antigens from hepatitis virus (Lancet 335 p1142, 1990). Heat killed or otherwise attenuated whole organism vaccines (Lancet 335 p898, 1990) would also be suitable for use with NAGO. Other examples include antigens from polio virus, cytomegalovirus, herpes simplex viru's, respiratory syncytial virus, rhinovirus, and Epstein Barr virus. Examples of animal viruses that would be compatible with NAGO include rabies, foot and mouth disease, equine 'flu, feline immunodeficiency and feline leukaemia virus (Lancet 335 p587, 1990).

Bacterial antigens such as from the following may advantageously be included in a vaccine formulation according to the present invention: *B. pertussis, C. tetani, E. coli, C. diphtheriae, P. Aeruginosa, V. cholerae, H. influenzae, N. meningitidis, S. pneumoniae, N. gonorrhea* and others with a suitable protein component or polysaccharide associated with a protein (*Bacterial Vaccines*, R. Germanier, ed., Academic Press Inc. New York, 1984).

In particular in relation to *B. pertussis*, the following components have been recognised as antigenic elements which may be used individually or in combination, when adjuvanted with NAGO, to provide an effective acellular vaccine against *B. pertussis* infections: filamentous haemagglutinin (FHA), P.69 (pertactin) and pertussis toxin (LPF) (*Bacterial Vaccines*, R. Germainier, ed. Chapter 3, *Pertussis*. Academic Press, New York, 1984). Antigens from parasites such as *P. falciparum* and *L. major* (Lancet 335 p1263, 1990) may also be adjuvanted by NAGO. Such an antigen is the principal malarial merozoite surface antigen.

Whilst alum will produce an adjuvant effect, our experiments show that NAGO is substantially more effective in producing antibody response in vivo. The potency of NAGO as an adjuvant raises the possibility of provoking undesirable, and unacceptable auto-immune responses to self-antigens. However, our experiments show this is highly unlikely since NAGO does not contravene the rules of genetically determined non-responsiveness. Thus, with influenza peptides of known MHC restrictions in mice, responses with NAGO as adjuvant occur when the MHC haplotype is permissive but not when it is non-permissive for a given peptide, even though regional lymph node lymphocyte numbers are increased in response to NAGO in the nonpermissive case.

The vaccine formulation may also comprise a suitable carrier, typically a conventional carrier for a vaccine for injection. NAGO is principally used in an aqueous diluent which may contain soluble or particulate antigens either alone or associated with a lipid carrier. NAGO may also be incorporated into water-in-oil emulsions and/or vehicles containing additional immunostimulatory elements such as muramyl dipeptide. Suitable amounts of vaccine formulations for injection into a patient are from 200 μl to 2ml and typically 500 μl (subcutaneous or intradermal for the smaller volumes, intramuscular for the larger).

The following examples serve to illustrate the present invention, but are not intended as a limitation thereof.

BRIEF DESCRIPTION OF THE DRAWINGS

In FIG. 3A the antigen concentration (μg/ml, x axis) is plotted against lymphocyte DNA synthesis ($^3$H-TdR incorporation, cpm× $10^{-3}$ se, y axis) and • denotes peptide 167 (10 μg), ■ denotes NAGO+a Balb/c T-cell epitope influenza A nucleoprotein peptide (171)(10 μg), ☐ denotes peptide 171 (10 μg) and o denotes no antigen.

In FIG. 3B the antigen concentration (μg/ml, x axis) is plotted against lymphocyte DNA synthesis ($^3$H-TdR incorporation, cpm× $10^{-3}$ se; y axis) and ■ denotes peptide 171+NAGO, o denotes peptide 171 and Δ denotes no antigen.

FIG. 10 shows T-cell priming to baculovirus-derived principal malarial merozoite surface antigen (rPMMSA) with NAGO, FCA, saponin or alum. The concentration of rPMMSA (μg/ml, x axis) is plotted against lymphocyte DNA synthesis ($^3$H-TdR incorporation, cpm×10$^{-3}$ se, y axis) and ▼ denotes NAGO+rPMMSA, ■ denotes FCA+rPMMSA, • denotes saponin+rPMMSA, ☐ denotes alum+rPMMSA, Δ denotes rPMMSA alone and ○ denotes no antigen.

In FIG. 13B peptide concentration (μg/ml, x axis) is plotted against lymphocyte DNA synthesis ($^3$H-TdR incorporation, cpm×10$^{-3}$ se, y axis), A denotes the response to the hybrid peptide, B denotes the response to the helper T-cell peptide composed of influenza A nucleoprotein amino acid residues 216 to 229, C denotes the response to the cytotoxic T-cell epitope peptide composed of influenza A nucleoprotein amino acid residues 147 to 169, • denotes NAGO+hybrid peptide, ☐ denotes saponin+hybrid peptide, ○ denotes FCA+hybrid peptide, ■ denotes alum+hybrid peptide and Δ denotes adjuvant alone.

EXAMPLE 1

Adjuvant Effects of Neuraminidase/Galactose Oxidase

Materials and Methods

Figure 1A:
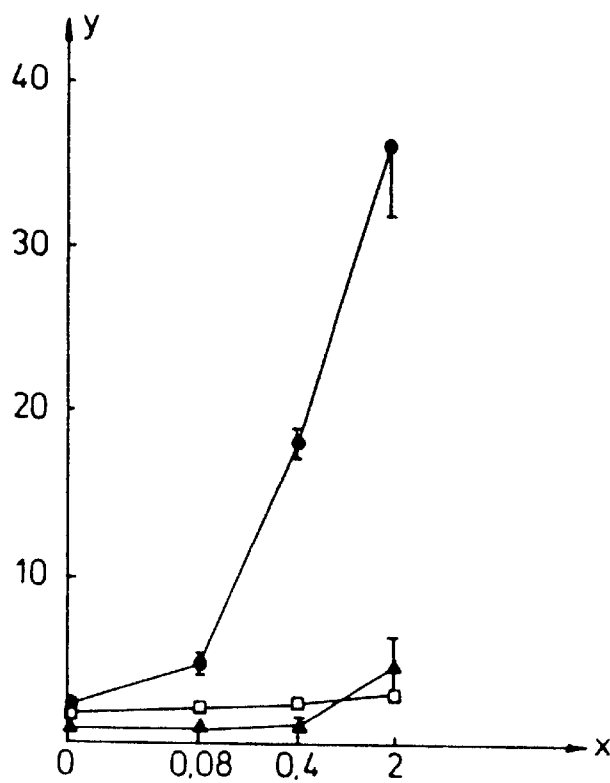
FIG. 1A shows the effects of NAGO on the response to keyhole limpet haemocyanin (KLH) in which the concentration of KLH in vitro (μg/ml; x axis) is plotted against lymphocyte DNA synthesis ($^3$H-TdR incorporation, cpm× $10^3$ se; y axis), • denotes 500 μg KLH+NAGO, ▼ denotes 500 μg KLH and ☐ denotes NAGO only.

T cell priming in regional lymph nodes. Mice were immunised by subcutaneous injection of antigen dorsally at the base of the tail. After seven days the regional distal (inguinal) lymph nodes were removed aseptically. A single cell suspension of lymph node cells was prepared by gentle homogenization of the tissue and the cells were washed and resuspended in click's medium containing 0.5% normal mouse serum at a concentration of 4×10$^6$ cells per ml. Aliquots of 100 μl were placed in each well of 96 well microtitre plates and 100 μl of medium containing antigen was then added. After three days cultures were pulsed with $^3$H-Thymidine (1 μCi per well). After a further 18h the cells were harvested onto glass microfibre filters and the degree of thymidine incorporation into DNA was measured by liquid scintillation spectrometry.

Antibody responses. Mice were immunized by subcutaneous injection of antigen dorsally at the base of the tail. Animals were bled after 21 days and the serum assayed for antibody by ELISA. 96-well, flat-bottomed plates were coated with antigen in carbonate buffer, pH 9.6 in a 100 μl volume for 24 h at 4° C. after which the plate was washed three times. Plates were blocked with 0.2% casein in phosphate buffered saline (200 μl per well, 2h 37°, followed by two washes). Serum samples diluted in PBS containing 0.05% tween 80 and 10% FCS were added (100 μl per well) and incubated for 2 h at 37°. The plates were then washed three times. Horse-radish peroxidase conjugated anti-mouse immunoglobulin antibody (Sigma Chemical Co. Poole Dorset, U.K.) at various concentrations (1/100–1/300 of commercial stock) in the same dilution buffer was then added (100 μl per well) and the plate incubated for 1–2h at 37°. The plate was then washed three times. Horse-radish peroxidase conjugated anti-mouse immunoglobulin antibody (Sigma Chemical Co. Poole Dorset, U.K.) at various concentrations (1/100–1/300 of commercial stock) in the same dilution buffer was then added (100 μl per well) and the plate incubated for 1–2h at 37°. The plate was then washed three times. Substrate solution containing tetramethyl benzidine and hydrogen peroxide in an acetate buffered solution was then added (100 μl per well) and the plate incubated for 10–30 minutes at 20° C. The reaction was halted with 1M sulphuric acid. OD at 450nm was then determined by means of an automated plate reader. Boosting of primed mice was performed intravenously and blood samples were taken after 7–12 days.

Results

1a T-cell Priming: NAGO Keyhole Limpet Haemocyanin

The data in FIG. 1A show the effects of NAGO (2.5u NA plus 5u GO) on the response to 500 μg keyhole limpet haemocyanin (Sigma Chemical Co., Poole, Dorset) when mixed with the Ag and given as a single subcutaneous dose.

1b&c T-cell Priming NAGO and Influenza Peptide 167

Figure 1B:
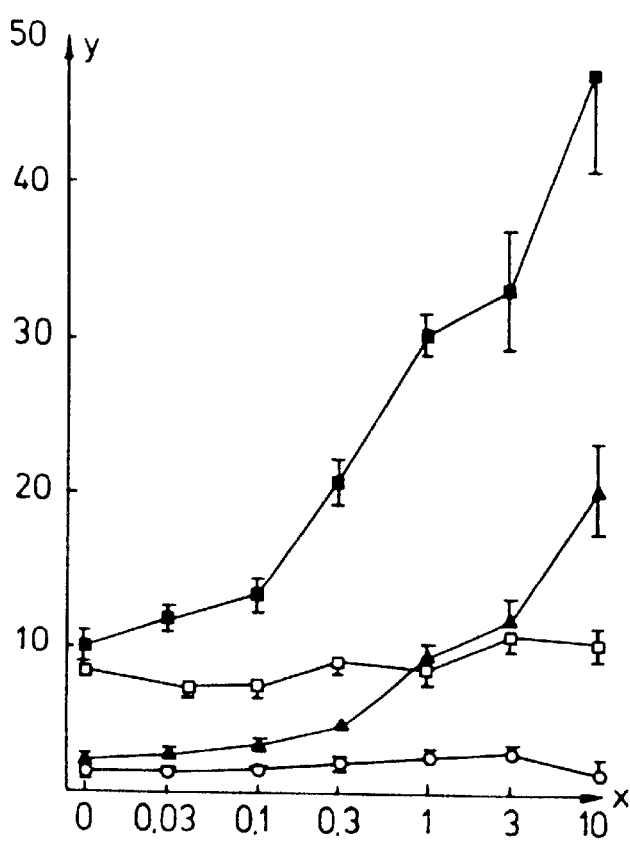
FIG. 1B shows the effects of NAGO on the response to a peptide (167) from the nucleoprotein of influenza A in which the concentration of antigen (μg/ml; x axis) is plotted against lymphocyte DNA synthesis ($^3$H-TdR incorporation, cpm× $10^{-3}$ se; y axis), ■ denotes peptide 167+NAGO, ▼ denotes peptide 167 only, ☐ denotes NAGO only and o denotes no antigen.
Figure 1C:
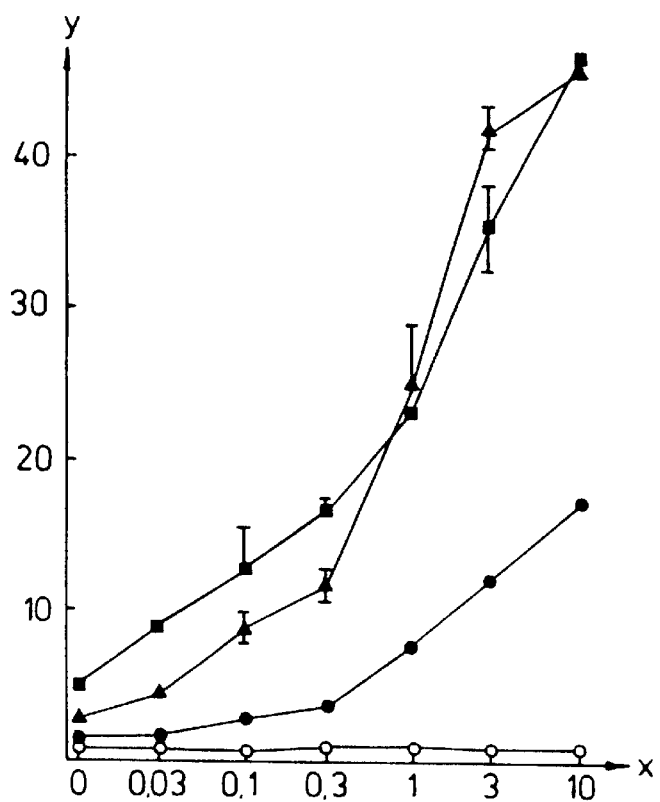
FIG. 1C shows the effects of GO and affinity-purified NA on the response to peptide 167 in which the concentration of antigen (μg/ml, x axis) is plotted against lymphocyte DNA synthesis ($^3$H-TdR incorporation, cpm× $10^{-3}$ se; y axis), ■ denotes crude NA+GO+peptide 167, ▼ denotes affinity purified NA+GO+peptide 167, • denotes peptide 167 only and o denotes no antigen.
Figure 1D:
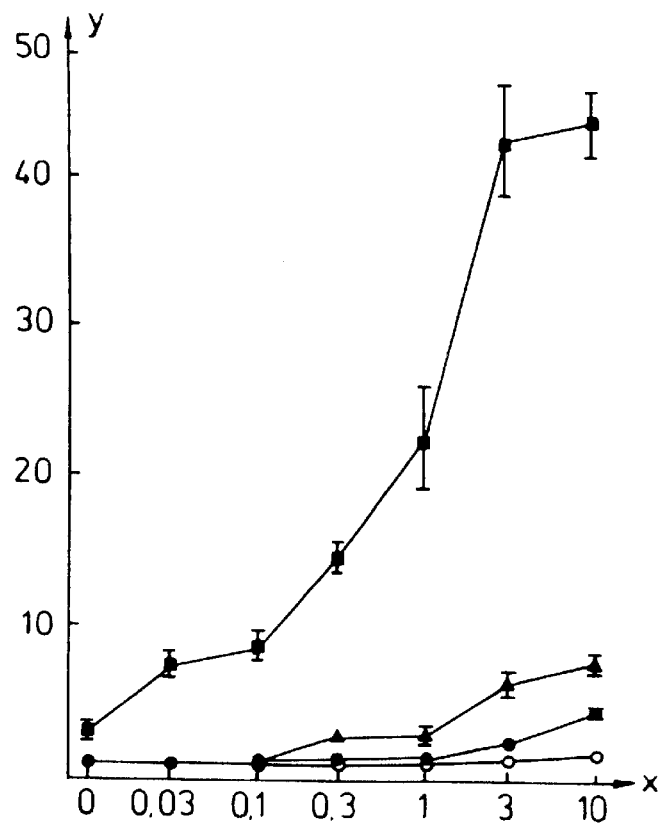
FIG. 1D shows the effects of heat inactivation of NAGO in which the concentration of antigen (μg/ml, x axis) is plotted against lymphocyte DNA synthesis ($^3$H-TdR incorporation, cpm× $10^{-3}$ se; y axis), ■ denotes NAGO+ peptide 167, ▼ denotes heat inactivated NAGO+peptide 167, o denotes peptide 167 only and o denotes no antigen.

The data in FIG. 1B show the same striking enhancement of T-cell priming in response to a peptide (167) from the nucleoprotein (NP) of Influenza A (defined as the major T-cell recognition antigen for NP in B10S mice). The same degree of enhancement was seen using affinity purified NA which has a 200-fold greater purity (FIG. 1C). Heat inactivation of NAGO prepared with the crude grade of NA completely abrogated the adjuvant effect as shown in figure 1D. These data rule out any contribution to the adjuvant effect from heat stable or heat labile bacterial contaminants present in the commercial grades of enzyme preparations.

EXAMPLE 2

Comparison of NAGO, Freund Complete Adjuvant and Aluminium Hydroxide

Figure 2:
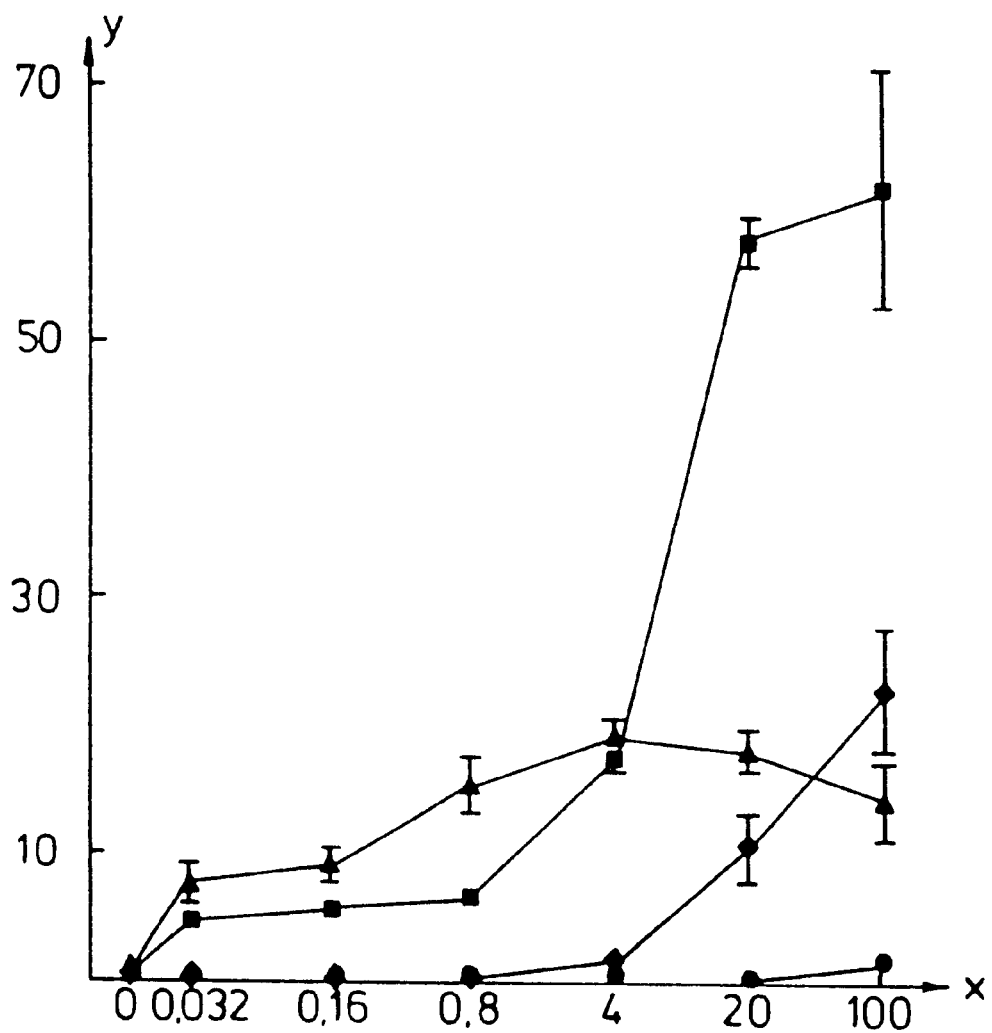
FIG. 2 shows a comparison of the addition to peptide 167 of NAGO (■), aluminium hydroxide (♦) and Freunds complete adjuvant (FCA, ▼) in which the concentration of antigen (μg/ml, x axis) is plotted against lymphocyte DNA synthesis ($^3$H-TdR incorporation, cpm× $10^{-3}$ se; y axis), • denotes peptide 167 only and o denotes no antigen.

The data in FIG. 2 compares the adjuvant effects of NAGO on the response to NP peptide 167 in B10S mice with that of aluminium hydroxide and Freund complete adjuvant (FCA). NAGO is strikingly superior to alum, and, at the higher concentrations of antigen used in the secondary challenge in vitro it is also markedly superior to FCA.

Figure 3A:
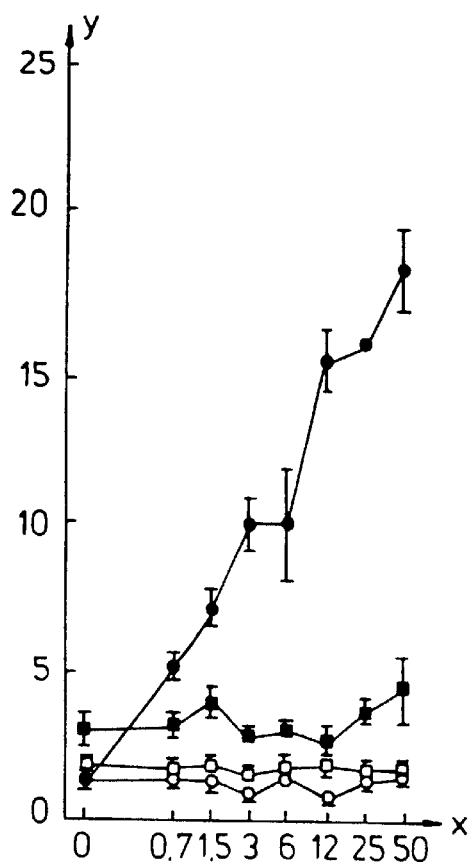
FIG. 3A shows that NAGO does not provoke a response to the BIOS epitope peptide 167 in Balb/c mice.
Figure 3B:
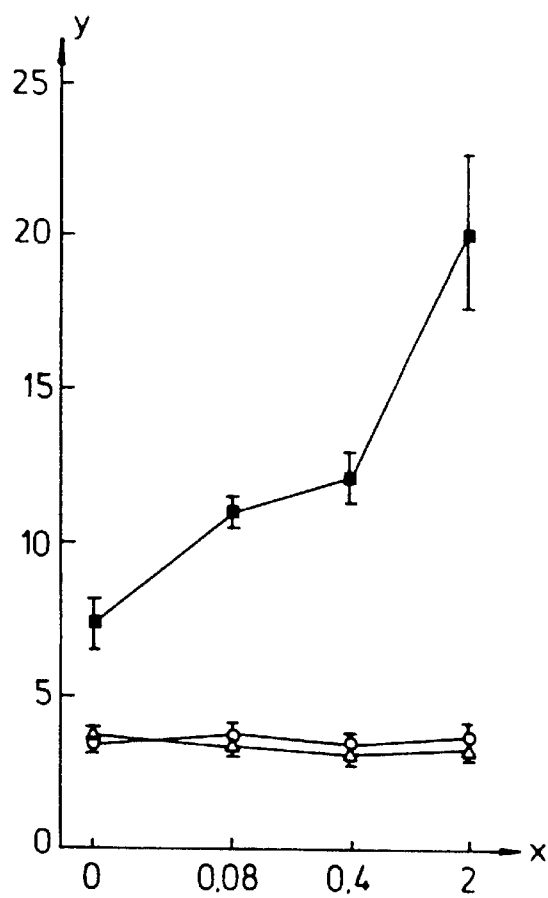
FIG. 3B shows that NAGO does adjuvant peptide 171 in Balb/c mice.

EXAMPLE 3
Demonstration that NAGO Does Not Violate Rules of Genetically Determined Non-responsiveness The potency of NAGO as an adjuvant raises the possibility of NAGO provoking unacceptable auto-immune responses to self-antigens. (i.e. self peptides occupying the groove of MHC class II molecules on accessory cells). This possibility is virtually ruled out by the data in FIG. 3A which show that NAGO does not violate the rules of genetically determined non-responsiveness in Balb/c mice. NAGO does not provoke a response to the B10S epitope NP167 in Balb/c mice. In contrast, NAGO does adjuvant the Balb/c T-cell epitope NP171 in these mice (FIG. 3B).

EXAMPLE 4
Antibody Responses

Figure 4:
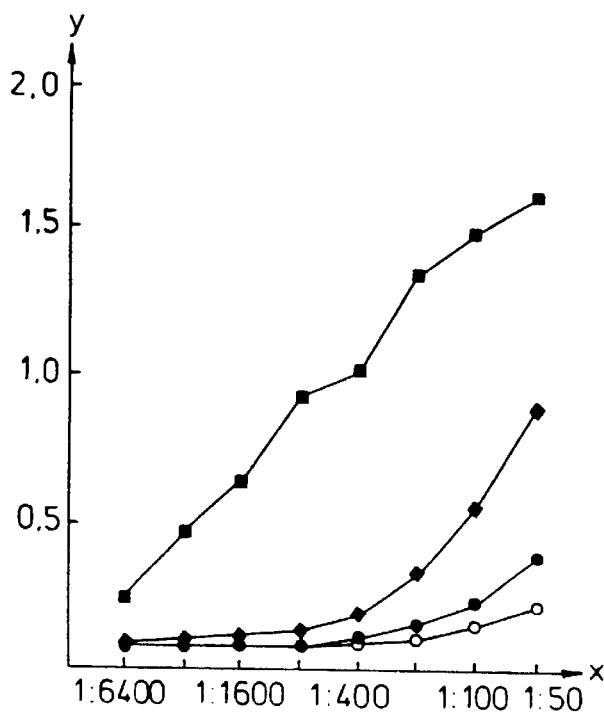
FIG. 4 shows the primary antibody response to ovalbumin in B10S mice where serum dilution (x axis) is plotted against optical density at 450 nm (OD 450 nm, y axis), ■ denotes ovalbumin+NAGO, ♦ denotes ovalbumin+alum, • denotes ovalbumin only and o denotes no antigen.

The data in FIG. 4 show the primary antibody response to the protein ovalbumin in B10S mice. NAGO provides a fifteen to twenty fold advantage over alum in terms of the dilution of antiserum containing an equivalent amount of antibody. Antibody responses to peptides were also adjuvanted by NAGO.

EXAMPLE 5
T cell Priming to HIV Antigen with NAGO

Figure 5:
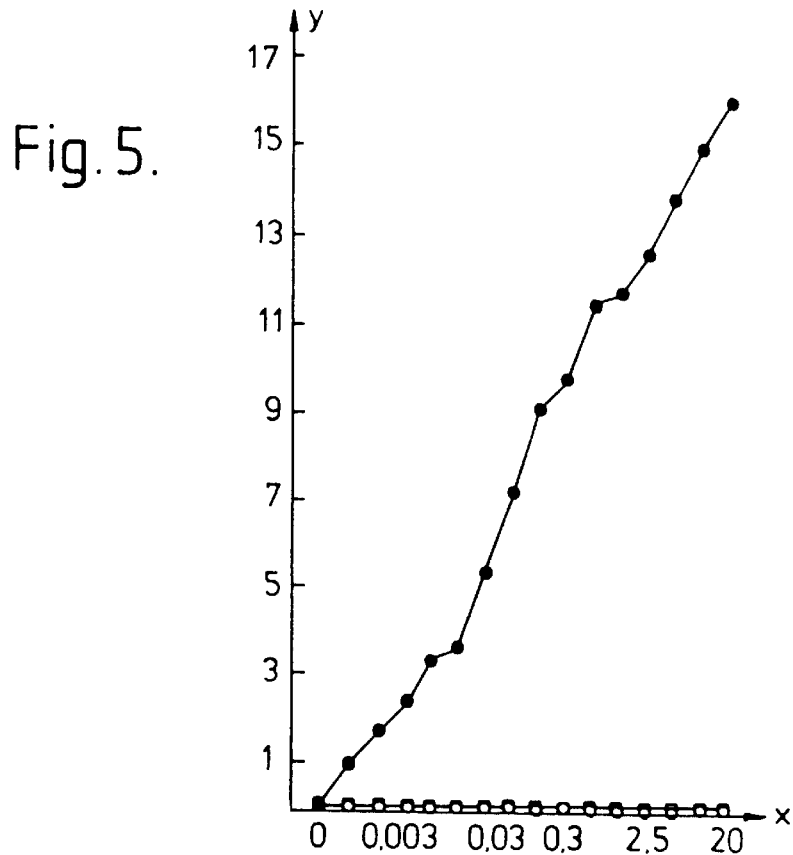
FIG. 5 shows T-cell priming to HIV gp120 with NAGO where the concentration of gp120 per ml (x axis) is plotted against lymphocyte DNA synthesis ($^3$H-TdR incorporation, cpm× $10^{-4}$ se, y axis), • denotes gp120+NAGO, ☐ denotes gp120 alone and o denotes no antigen.

The data in FIG. 5 show T cell priming to the HIV envelope Antigen (Ag) gp120. No priming occurred with Ag alone but a potent adjuvant effect was achieved with NAGO. B10S mice received 1 µg of gp120 (from baculovirus) subcutaneously at the base of the tail with or without the standard dose of NAGO. Seven days later the regional (inguinal) lymph nodes were removed and the lymph node cells restimulated in vitro with gp120 at the concentrations shown. Lymphocyte DNA synthesis was measured after a further 4 days.

Figure 6A:
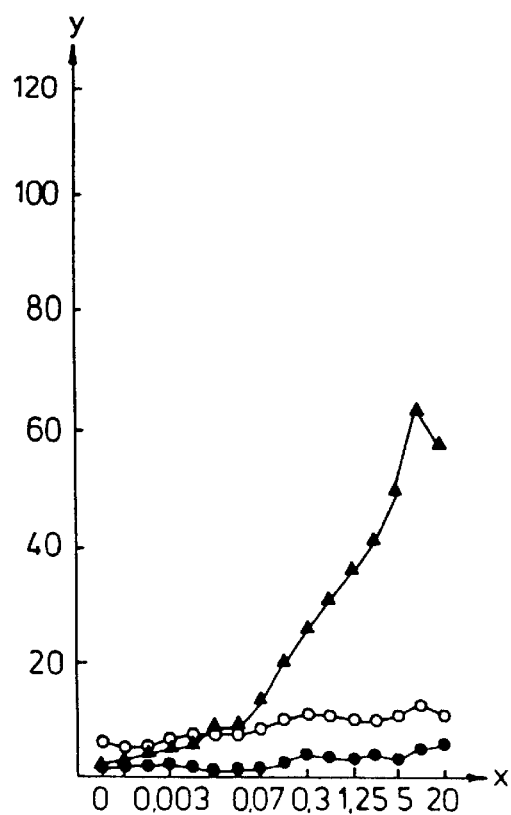
FIG. 6A shows T-cell priming to the P69 subunit of pertussis with NAGO where the concentration of P69 (μg/ml, x axis) is plotted against lymphocyte DNA synthesis ($^3$H-TdR incorporation, cpm× $10^{-3}$ se, y axis), ▼ denotes P69+NAGO, • denotes P6 alone and o denotes no antigen.
Figure 6B:
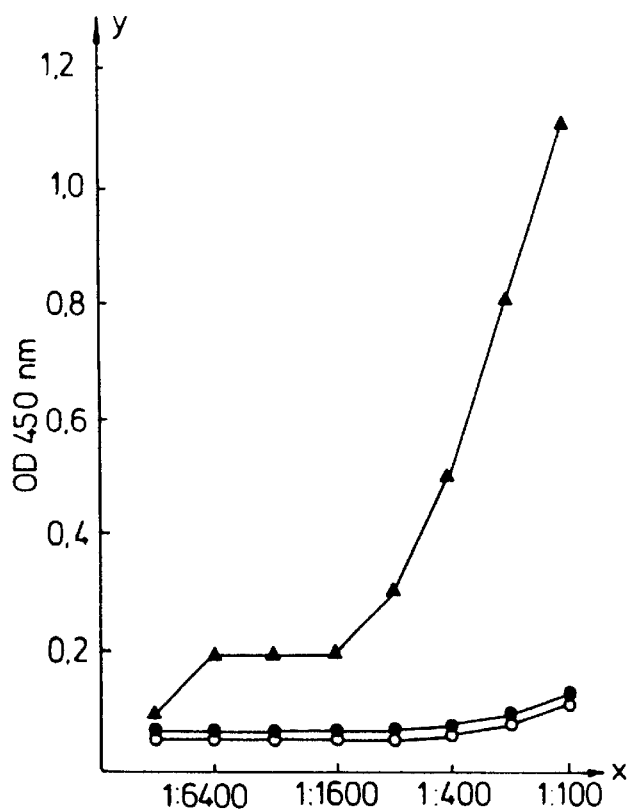
FIG. 6B shows antibody response to P69 where serum dilution (x axis) is plotted against OD 450 nm (y axis), ▼ denotes P69+NAGO, • denotes P69 alone and o denotes control.

EXAMPLE 6
T cell Priming and Antibody Responses to the P69 (pertactin) Subunit of Pertussis with NAGO The data in FIG. 6a show T cell priming to p69 of pertussis. No priming occurred with the Ag alone but a potent adjuvant effect was achieved with NAGO. B10S mice received 1 µg of p69 (from Pichia pastoralis) subcutaneously at the base of the tail with or without the standard dose of NAGO. Seven days later the regional (inguinal) lymph nodes were removed and the lymph nodes restimulated in vitro with p69 at the concentrations specified. Lymphocyte DNA synthesis was measured after a further 4 days. The data in FIG. 6b show the serum IgG antibody response of B10S mice immunised with p69 in just the same way. Serum was sampled 14 days after a single subcutaneous injection of 1 µg of p69. Substantial amounts of antibody were induced by NAGO but not by Ag alone.

EXAMPLE 7
Induction of Cytotoxic T cells (CTL) by NAGO

Figure 7:
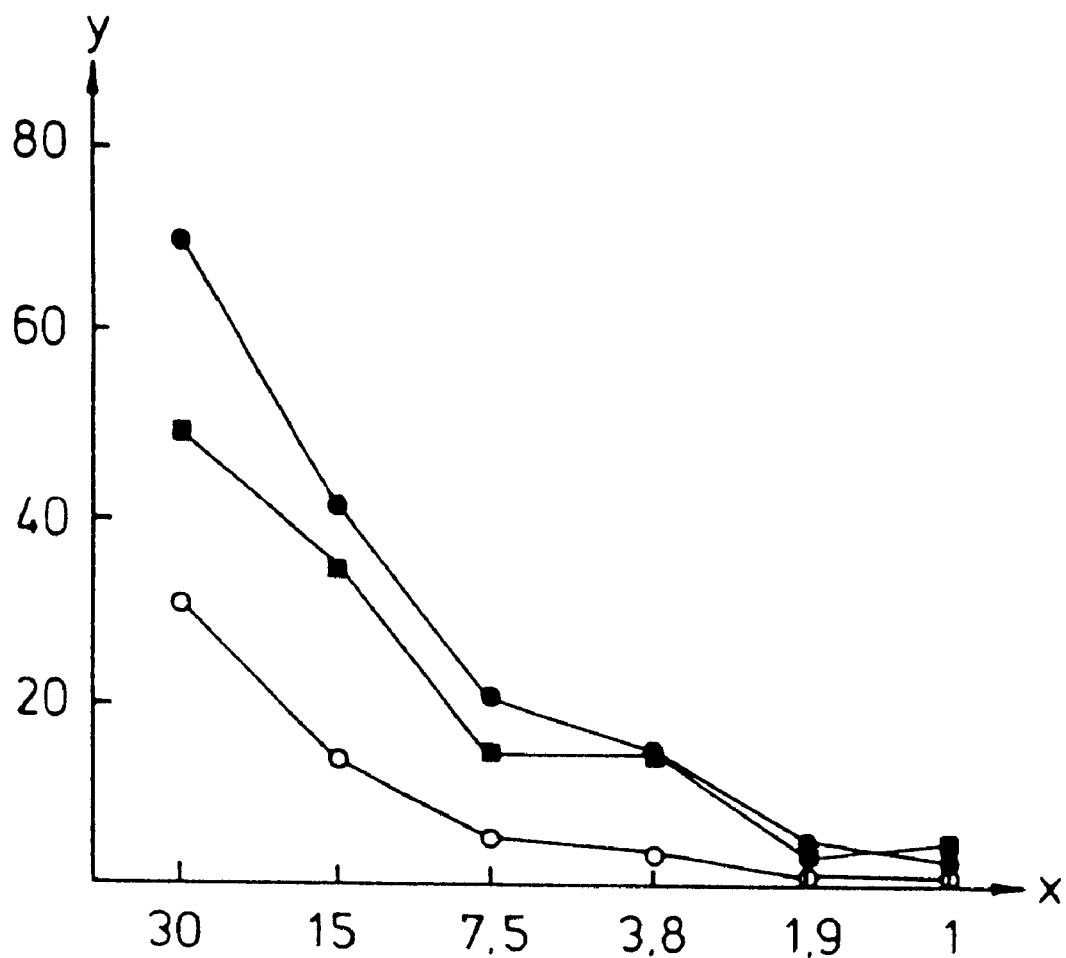
FIG. 7 shows the induction of cytotoxic T cells by NAGO where the effector:target ratio (x axis) is plotted against the percentage of total $^{51}$Cr released from detergent-lysed cells which had been pulsed with influenza peptide p110(•) or with influenza virus PR8 (■) or which had not be pulsed with antigen.

In addition to humoral immunity, cell-mediated effector mechanisms are an important defence mechanism particularly in relation to viral infections. Conventional adjuvants such as alum do not induce cytotoxic T cells. In contrast NAGO was found to induce such CTL. The data in FIG. 7 show the killing of target cells expressing viral antigens by cytotoxic T cells from mice immunised with an influenza peptide using NAGO as adjuvant. Mice received the peptide p110 together with the standard dose of NAGO subcutaneously and were boosted with the same material five weeks later. After a further seven weeks spleens were harvested and the spleen cells restimulated in vitro with peptide for 5 days. Target cells (the P851-J cell line) were pulsed with peptide or with PR8 influenza virus and labelled with $^{51}$Cr. Killing of target cells during a six hour incubation was measured by release of $^{51}$Cr expressed as a percentage of the total released from detergent-lysed cells. Killing was measured as a function of the effector:target cell ratio.

EXAMPLE 8
Comparison of NAGO with Freund Complete Adjuvant in T-cell Responses to the gp120 Subunit of Human Immunodeficiency Virus (HIV)

Figure 8A:
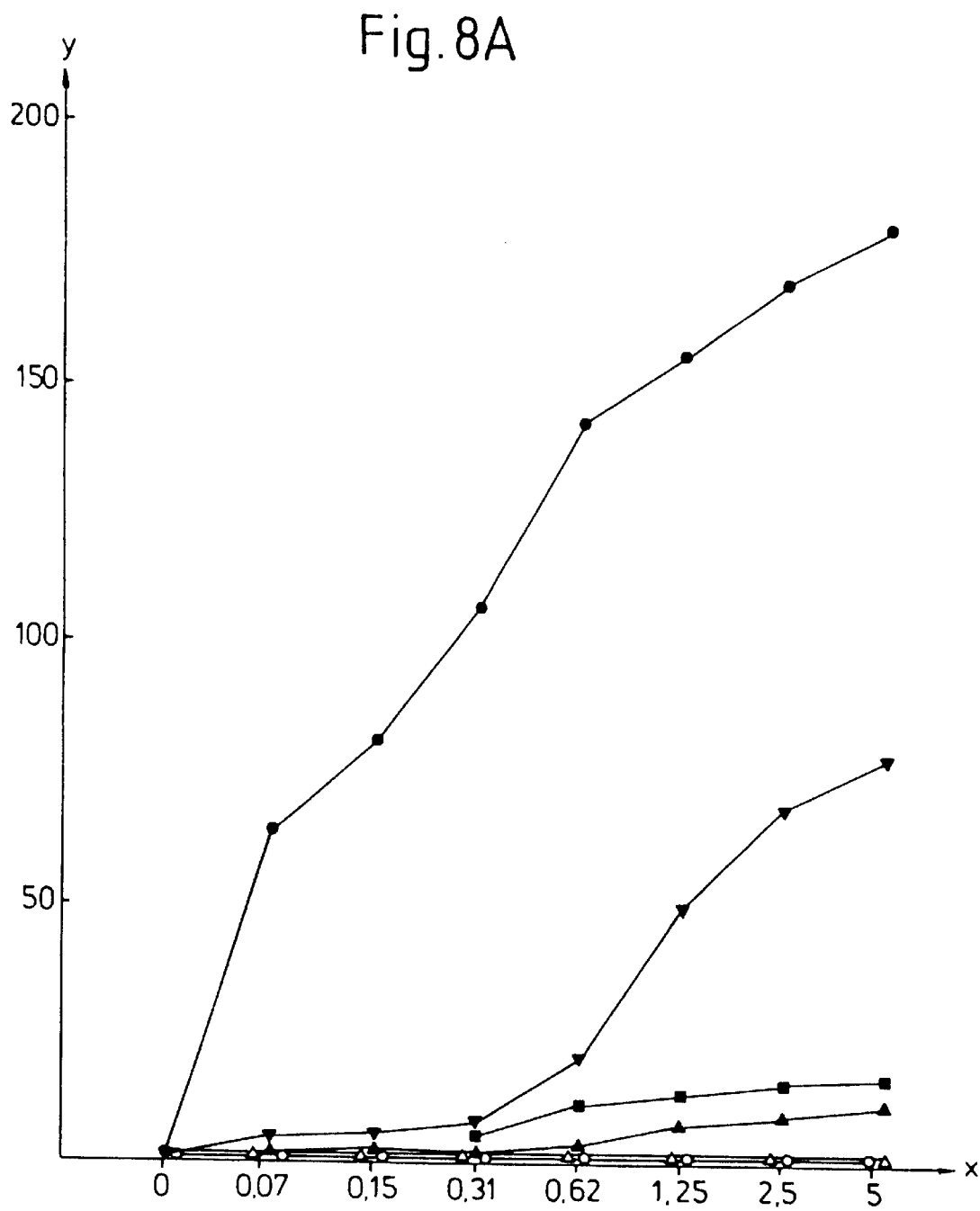
FIG. 8A shows the response of T-cells from mice immunised with HIV gp120 expressed in a baculovirus system (gp120 bac) with NAGO or FCA. The concentration of gp120(μg/ml, x axis) is plotted against lymphocyte DNA synthesis ($^3$H-TdR incorporation, cpm× $10^{-3}$ se; y axis) and • denotes NAGO+gp120 bac restimulated with gp120 bac, ▲ denotes NAGO+gp120 bac restimulated with gp120 expressed in Chinese hamster ovary cells (gp120 CHO), ■ denotes FCA+gp120 bac restimulated with gp120 bac, ▼ denotes FCA+gp120 bac restimulated with gp120 CHO, Δ denotes gp120 bac restimulated with gp120 bac and o denotes gp-120 bac restimulated with gp120 CHO.

Having established that NAGO was effective in priming T-cells to the gp120 envelope glycoprotein subunit of HIV, NAGO was directly compared in this respect with the strong conventional adjuvant Freund complete adjuvant (FCA). The latter, a non-metabolisable oil adjuvant which contains killed mycobacteria, is too aggressive for human use and has a tendency to produce chronic granulomas which do not resolve. For the comparison, gp120 expressed in a baculovirus system (gp120 bac from American Biotechnologies Inc.) or in Chinese hamster ovary cells (gp120 CHO from Celltech Ltd.) were used as antigens (the former has much less glycosylation). The data in FIG. 8A show the response of T-cells from animals immunised with gp120 bac. with NAGO (1u NA+Su GO) or with the standard dose of FCA.

Figure 8B:
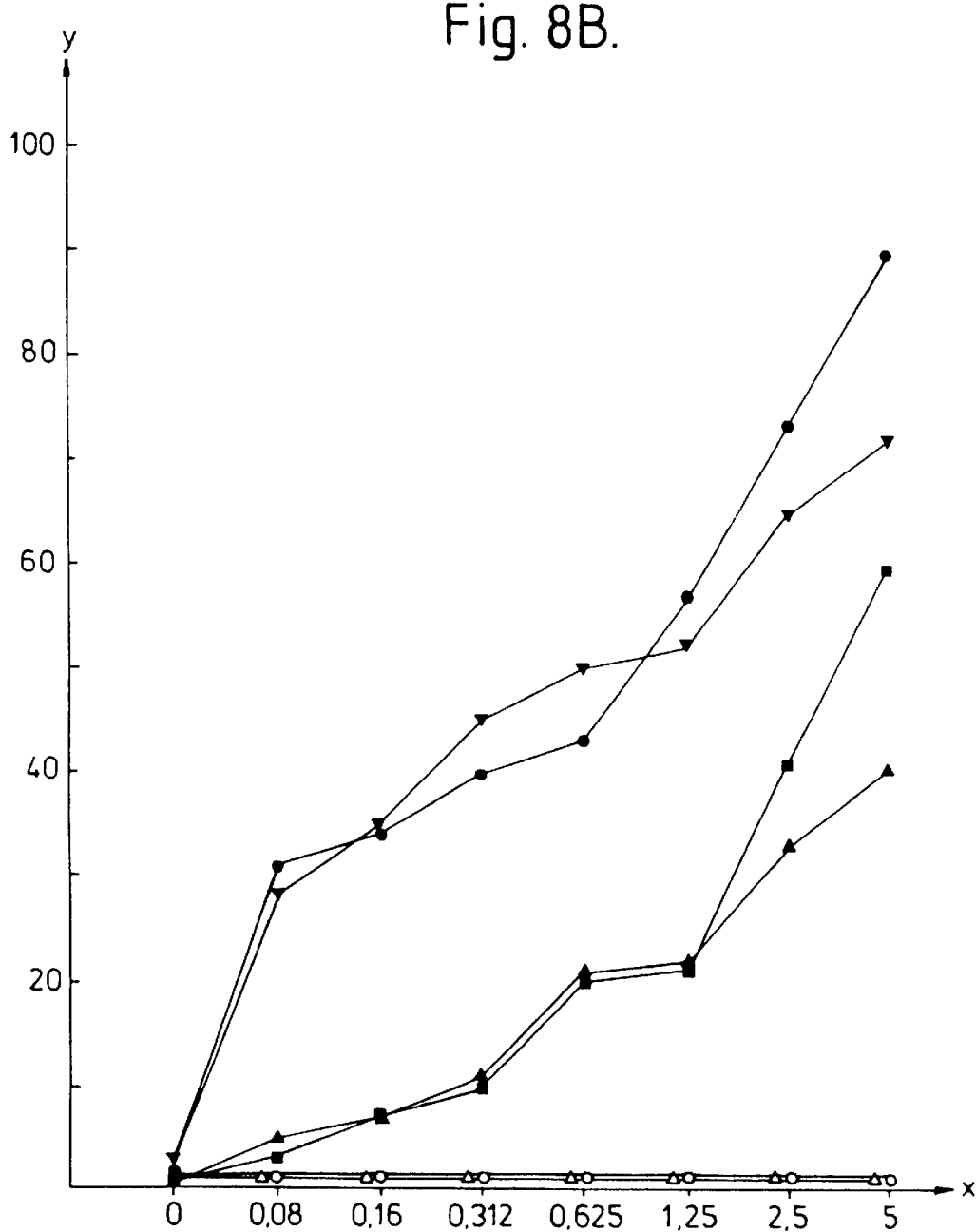
FIG. 8B shows the response of T-cells from mice immunised with gp120 CHO with NAGO or FCA. The concentration of gp120 (μg/ml, x axis) is plotted against lymphocyte DNA synthesis ($^3$H-TdR incorporation, cpm× $10^{-3}$ se, y axis) and • denotes NAGO+gp120 CHO restimulated with gp120 CHO, ▲ denotes NAGO+gp120 CHO restimulated with gp120 bac, ■ denotes FCA+gp120 CHO restimulated with gp120 CHO, ▼ denotes FCA+gp120 CHO restimulated with gp120 bac, Δ denotes gp120 CHO restimulated with gp120 CHO and o denotes gp120 CHO restimulated with gp120 bac.

Mice received 1 µg of gp120 subcutaneously in the dorsal mid-line at the base of the tail. After 7 days regional (inguinal) lymph nodes were removed in the standard procedure and the cells restimulated in vitro with gp120 bac or gp120 CHO. In this system NAGO produced a remarkable 5–10 fold increase in the T-cell response compared with FCA. In the same way, the T-cell response of mice immunised with 1 µg of gp120 CHO with NAGO or FCA as adjuvant are compared in FIG. 8B. T-cells were restimulated with either gp120 CHO or gp120 bac. Here, NAGO conferred a 2-fold advantage over FCA.

Figure 9A:
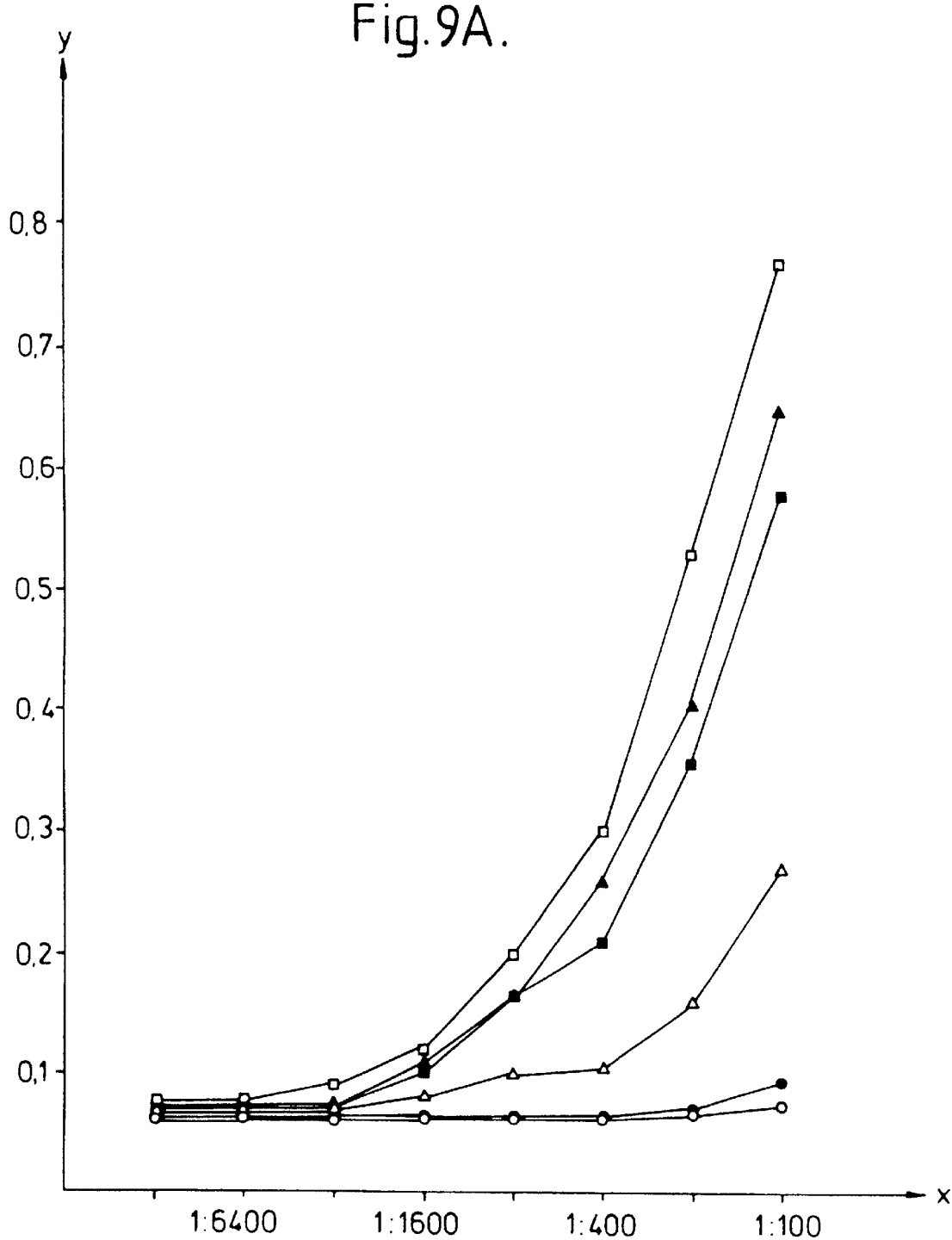
FIG. 9A shows the antibody response to gp120 CHO where serum dilution (x axis) is plotted against OD 450 (y axis), ■ denotes NAGO+gp120 CHO, ☐ denotes FCA+ gp120 CHO, ▼ denotes saponin+gp120 CHO, Δ denotes alum+gp120 CHO, o denotes gp120 CHO alone and • denotes no antigen.
Figure 9B:
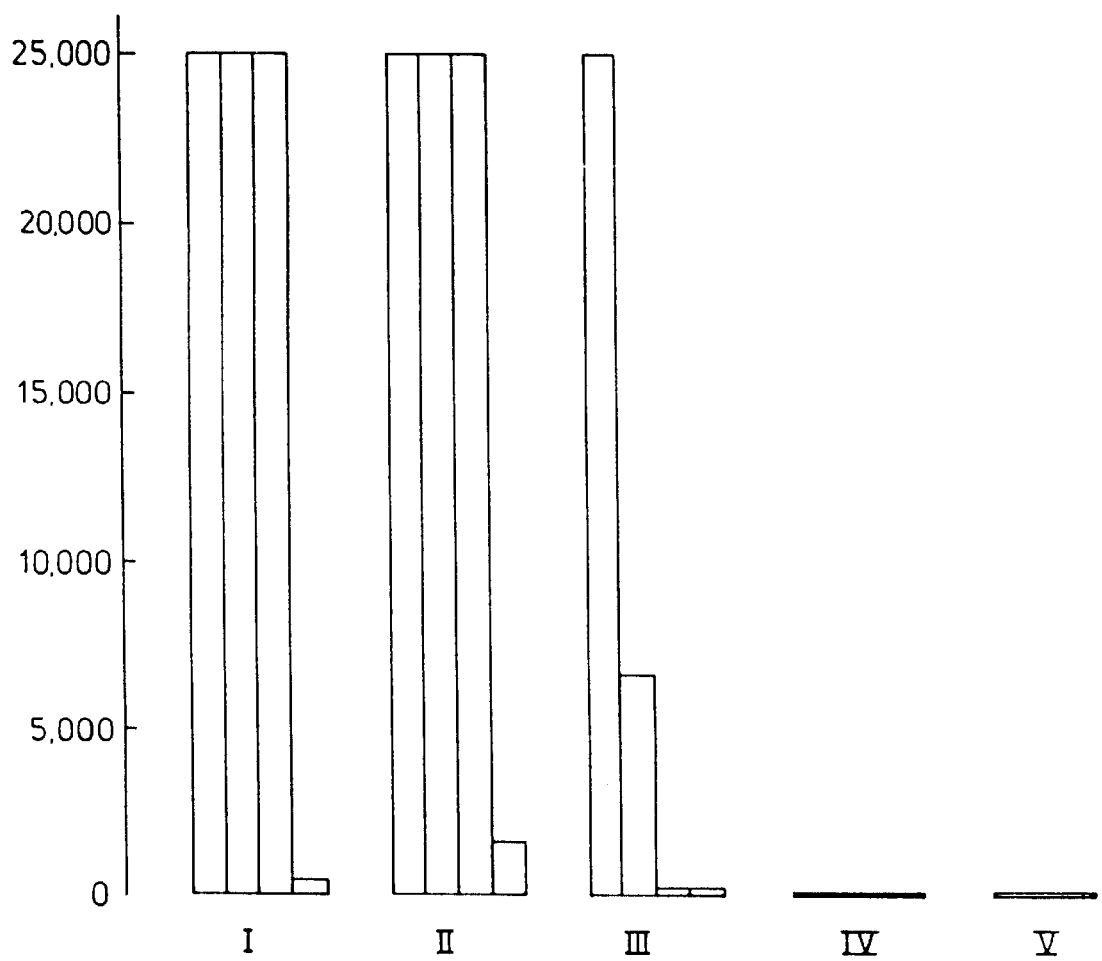
FIG. 9B compares IgG antibody titres for (I) FCA, (II) saponin, (III) NAGO, (IV) alum and (V) no adjuvant.

EXAMPLE 9
Comparison of NAGO with Freund Complete Adjuvant, Alhydrogel (Alum), and Saponin in the Induction of Primary and Secondary Antibody Responses to the pg120 Subunit of HIV CBA mice were immunized with 1 µg of gp120 CHO together with one of the following adjuvants: alhydrogel (100 µg), saponin (50 µg) or FCA (standard dose of 50 µl Ag solution emulsified with an equal volume of FCA). Serum was sampled after 2 weeks and pooled within groups. Antibody to gp120 was then determined by ELISA. The data in FIG. 9A show that NAGO was markedly superior to alhydrogel (the standard adjuvant for human use) and was comparable in effectiveness to saponin. FCA was slightly more effective in this primary response. Twelve weeks after the first immunisation mice were boosted using the same protocol as in priming (1 µg gp120 CHO+adjuvant). Serum was harvested one week later and antibody levels were determined by ELISA. End point titres are shown in FIG. 9B. Alum (the standard human adjuvant) induced neglible amounts of anti-gp120 antibody. In contrast, NAGO produced high titres in 2 out of four mice, comparable to those produced by saponin and FCA.

EXAMPLE 10
Comparison of NAGO with Freund Complete Adjuvant, Saponin and Alum in the Priming of T-cells to Baculovirus-derived Principal Malarial Merozoite Surface Antigen (rPMMSA).

B10S mice were immunised with 2 μg of the candidate malarial vaccine antigen rPMMSA with the following adjuvants: alum (100 μg), saponin (50 μg) FCA.(standard dose), or NAGO (1 unit NA+5 units GO). Lymph node cells were obtained after 7 days by the standard procedure and restimulated with rPMMSA. The data in FIG. 10 show that strong T-cell priming occurred with NAGO and with FCA and that these two agents were broadly comparable, whereas only weak priming occurred with saponin and no significant priming with alum.

EXAMPLE 11

Figure 11:
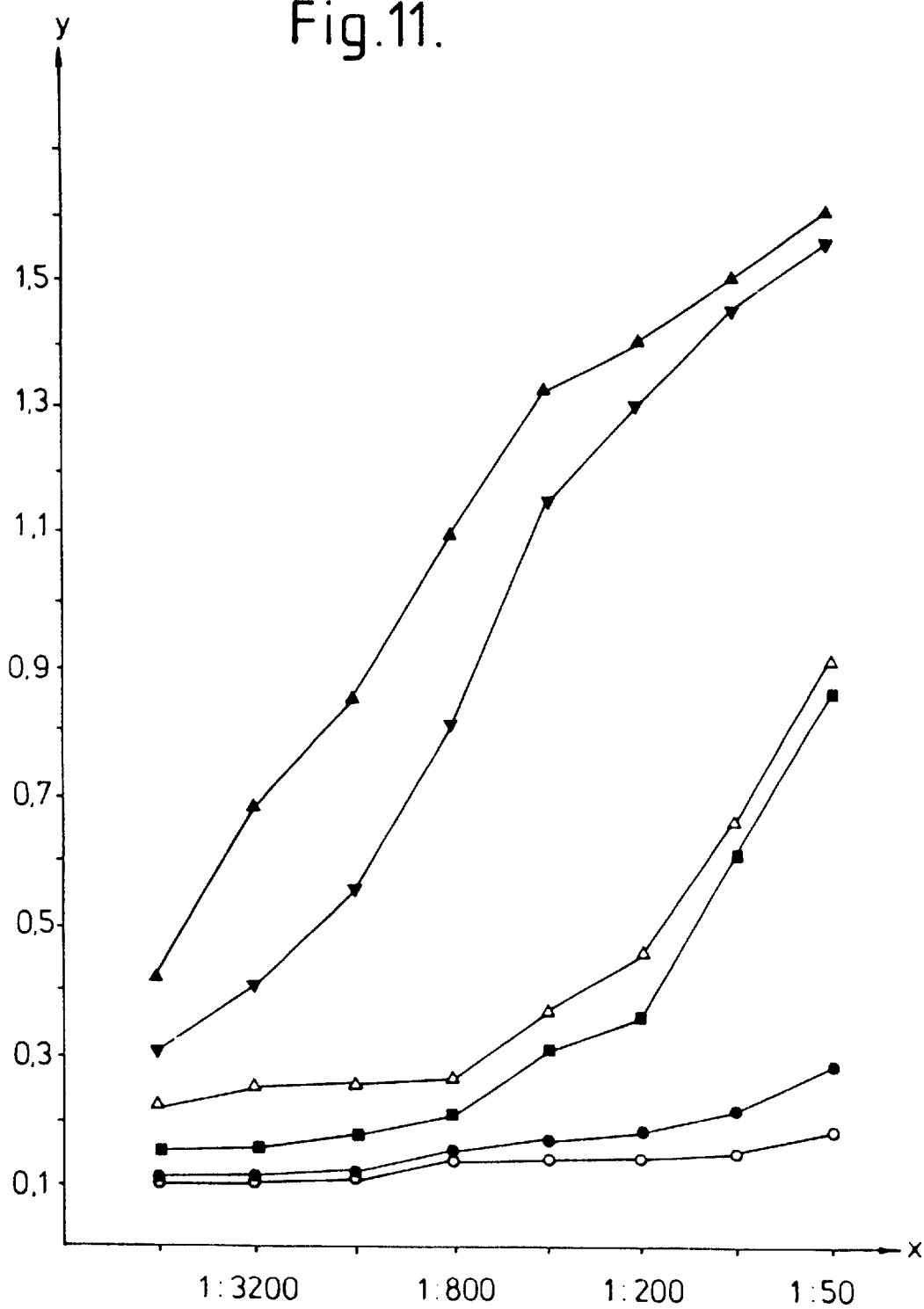
FIG. 11 shows the antibody response to rPMMSA where serum dilution (x axis) is plotted against OD 450 (y axis), Δ denotes NAGO+rPMMSA, ▼ denotes FCA+rPMMSA, ▲ denotes saponin+rPMMSA, ■ denotes alum+rPMMSA, ○ denotes rPMMSA alone and ○ denotes no antigen.

Comparison of NAGO with Freund Complete Adjuvant, Saponin and Alum in the Primary Antibody Response to rPMMSA B10S mice received 2 μg rPMMSA with the standard dose of the four adjuvants as in example 10. Serum was sampled after 2 weeks. Here, NAGO produced a substantial adjuvant effect comparable to that of alum. Saponin and FCA produced stronger responses to this antigen. The data are shown in FIG. 11.

EXAMPLE 12

Comparison of NAGO with Alhydrogel in Priming for an Antibody Response to Group B Meningococcal Vaccine (MB6400).

Figure 12:
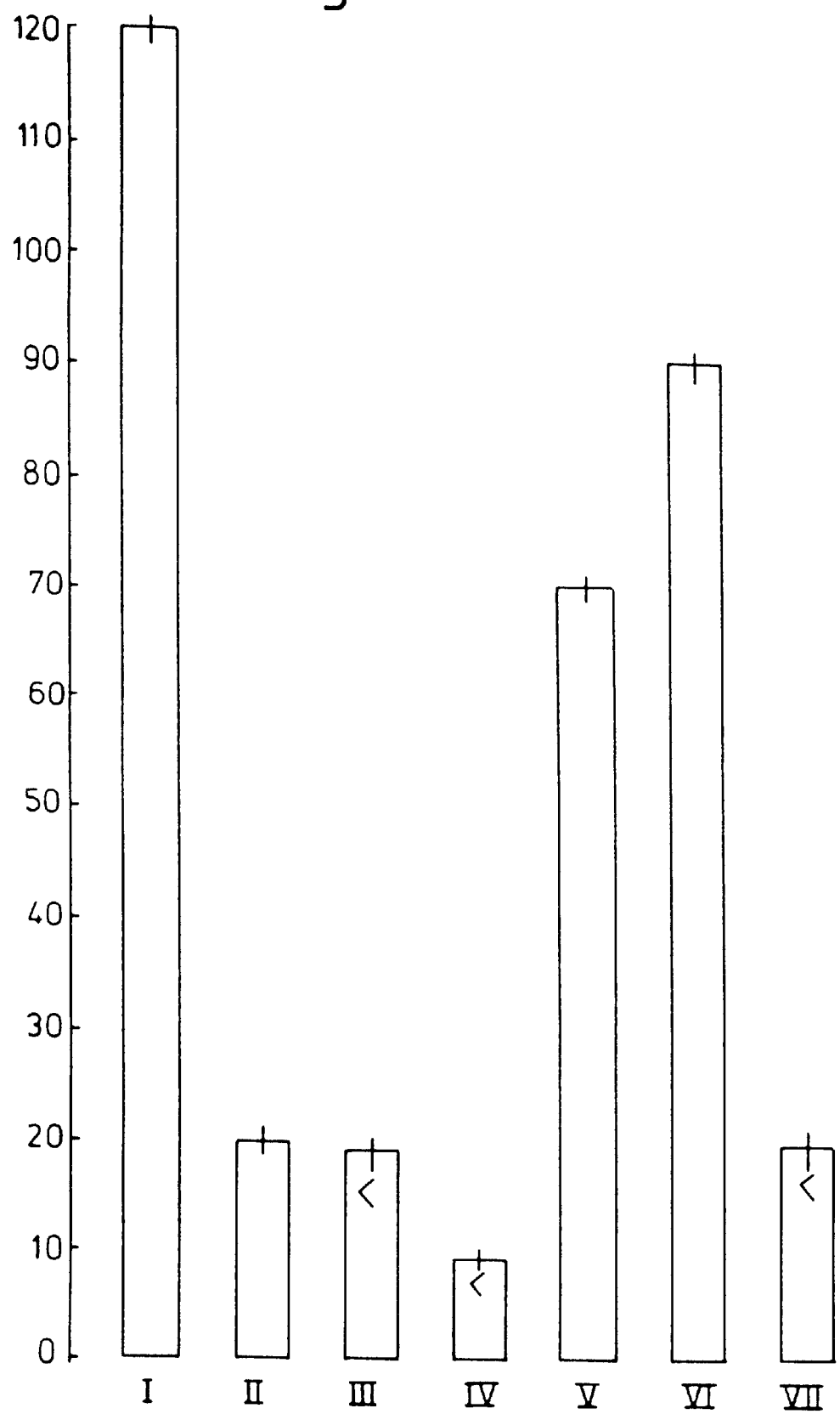
FIG. 12 shows the antibody response to meningococcal vaccine MB6400. Specific antibody to meningococcal polysaccharide (μg per ml of serum) is noted for (I) vaccine+NAGO, (II) vaccine+alhydrogel, (III) vaccine alone, (IV) NAGO alone, (V) vaccine+GO, (VI) vaccine+NAGO given 1 hour earlier and (VII) unimmunised.

Mice received a primary subcutaneous immunization with 0.1 ml of the group B meningococcal vaccine MB6400 in phosphate buffered saline with or without adjuvant. The standard dose of alhydrogel (100 μg) was compared with the standard dose of NAGO (1 unit NA+5 units GO). One group received GO (5 units) with the vaccine. Another group received NAGO 1 hour before the vaccine. Control groups received vaccine alone or adjuvant alone. Each dose of vaccine consisted of 10 μg of protein covalently linked to polysaccharide. Twenty-eight days later all mice received a secondary s.c. immunisation with vaccine with 100 μg of alhydrogel. Serum was sampled 7 days later and assayed by enzyme-linked immunosorbent assay (ELISA) for specific anti-polysaccharide antibody. The results are expressed as the weight of specific antibody per unit volume of serum and are shown in FIG. 12. NAGO produced a five-fold advantage over alhydrogel.

EXAMPLE 13

Comparison of NAGO with Saponin, Alum and Freund Complete Adjuvant in the Induction of Cytotoxic T-cells Recognising Influenza Antigens.

NAGO is very potent in inducing T-cell proliferative responses (comparable or better than FCA), but this is not fully reflected in its efficacy in inducing antibody (generally somewhat less effective than FCA or saponin). The function of T-cells is to help in the production of antibody and to make cytotoxic responses against virally infected cells. It therefore seemed likely that the T-cell response induced with NAGO is biased towards the induction of cytotoxic T-cells. This was tested using peptides from the nucleoprotein of Influenza A. BALB/c mice were primed subcutaneously with 100 μg of a hybrid peptide containing a dominant cytotoxic T-cell (CTL) epitope (aa147–169) linked to a major T-helper cell epitope (216–229) for this strain of mice. The standard dose of adjuvant was used in each case (FCA 1:1 vol/vol, saponin 50 μg, alum 100 μg or NAGO 1 u NA+5u GO). Three weeks later mice were boosted s.c. with the same dose of peptide in the same adjuvant (except the FCA group which received Freund incomplete adjuvant without mycobacteria to mimimise the granulomatous response). Control mice received peptide or adjuvant alone. The response in all groups was compared with mice infected intra-nasally with live A/PR8 virus.

The procedure was as follows: At least three weeks after the second immunization, spleens were removed and spleen cells were stimulated in vitro with either PR8 infected spleen cells or spleen cells pulsed with the homologous immunising peptide or untreated spleen cells. CTL generation was measured 5 days later using $^{51}$Cr release from labelled P815 tumour cells which had been either infected with PR8 virus or pulsed with the peptide aa147-160 (the peptide recognised by CTL), or were untreated as a control. Thus there are nine sets of data—cells were restimulated in vitro in three ways, (with virus-infected, peptide-pulsed or untreated spleen cells), and for each of these there were three types of targets—virus infected, peptide-pulsed or untreated P815-5 cells.

Figure 13A:
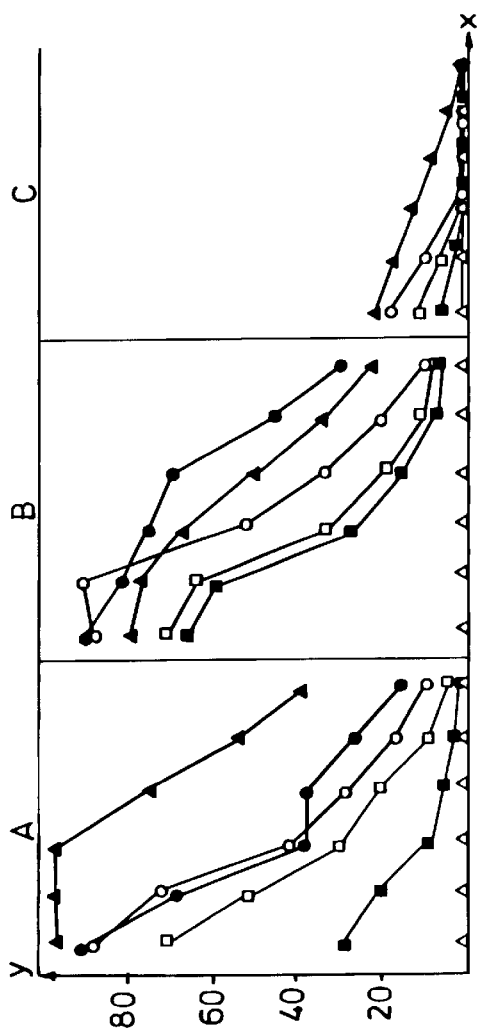
FIG. 13A compares the induction of cytotoxic T cells by NAGO, FCA, saponin or alum where the effector target cell ratio (x axis) is plotted against specific lysis ($^{51}$Cr release, %; y axis) of cells which had been pulsed with (a) influenza virus PR8 or (b) a hybrid peptide composed of amino acid residues 147 to 169 of the nucleoprotein of influenza A linked to residues 216 to 229 of the nucleoprotein of influenza A or which had been untreated (c). In the figure ▼ denotes live virus infection, • denotes NAGO+hybrid peptide, ○ denotes FCA+hybrid peptide, ☐ denotes saponin+hybrid peptide, ■ denotes alum+hybrid peptide and Δ denotes adjuvant alone.
Figure 13A:
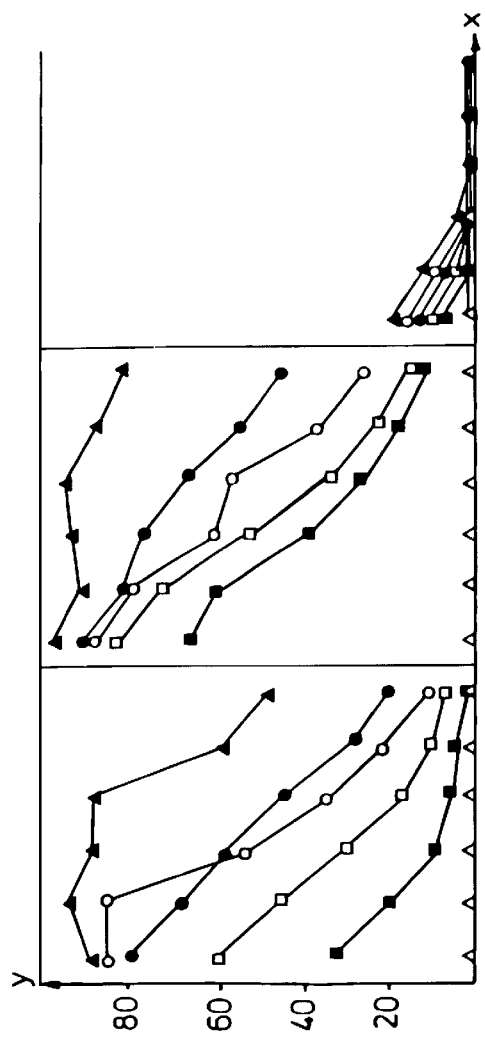
Figure 13A:
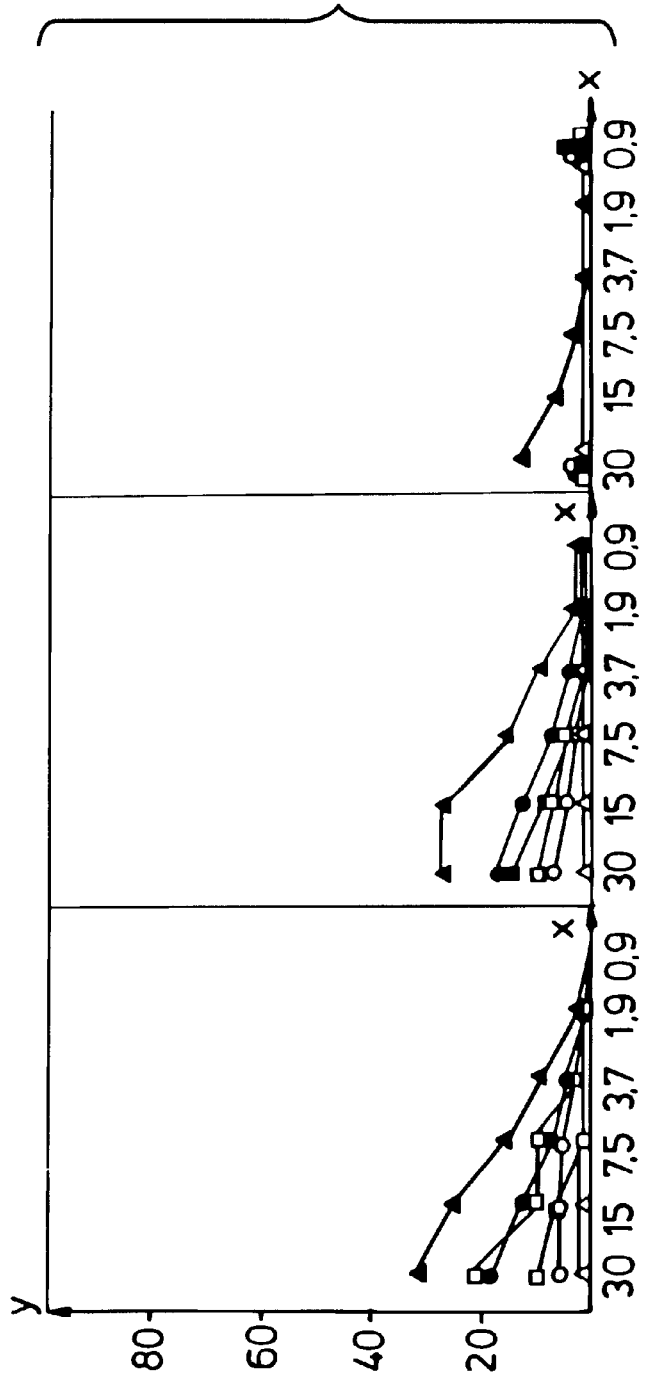

The data are shown in FIG. 13A. Vertical column A shows responses following in vitro stimulation with virus-infected spleen cells on the three targets: virus-infected targets (a), peptide-pulsed targets (b), or untreated targets (c). Vertical column B shows responses following in vitro stimulation with peptide-pulsed spleen cells on the same three targets. Vertical column C shows responses following in vitro stimulation with normal spleen cells on the same three targets.

The data in column A show that, not surprisingly, intranasal infection with live virus is the most potent way to prime CTL for restimulation in vitro with virus infected cells. Nevertheless, very good priming with peptide is also achieved with FCA and NAGO, and the two are comparable. Saponin also primes well with peptide but is slightly less effective. Significant priming with peptide was also seen with alum but this was much less effective than the other three adjuvants. A similar picture was obtained with peptide-pulsed targets. The bottom figure shows non-specific release of $^{51}$chromium from Ag-negative target cells.

The data in column B show that in priming T-cells for restimulation in vitro with peptide-pulsed spleen cells, NAGO is more potent than FCA, saponin or alum. This was the case with both virus- and peptide-pulsed targets. In the case of virus infected targets, NAGO+peptide even displaced live virus infection as the most potent primer for restimulation with peptide-pulsed spleen cells. The data in column C show that in the absence of secondary stimulation in vitro no significant cytotoxicity is detectable.

The cytotoxic T-lymphocytes demonstrated here were inhibited by anti-CD8 antibody but not by anti-CD4 antibody. They lysed MHC class I positive but not class II positive target cells. This indicates that they are conventional class I-restricted CD8+CTL. Such cells are likely to be principal mediators of protection against viral infection. It is also important to note that NAGO was an effective adjuvant in the induction of peptide specific CTL that recognise cells infected with live virus. This, of course, is a requisite of any peptide-based vaccine.

Figure 13B:
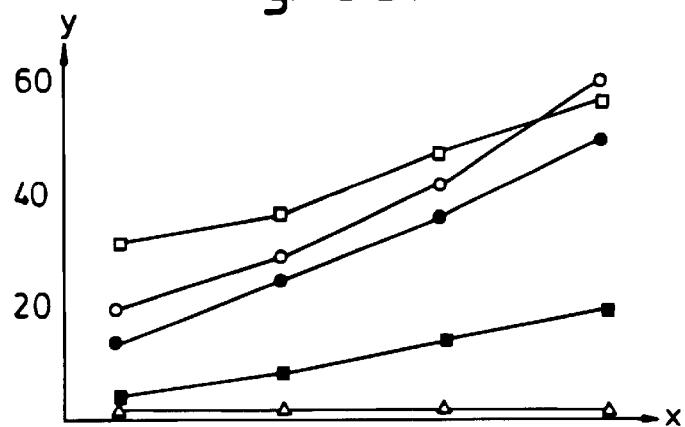
FIG. 13B shows the proliferative responses in mice immunised for cytotoxic T cell generation.
Figure 13B:
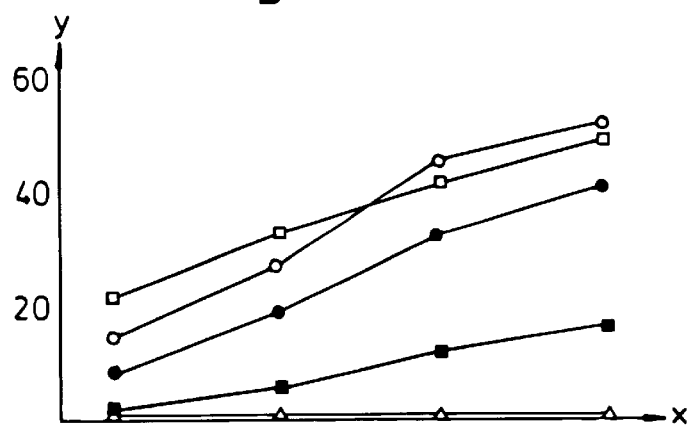
Figure 13B:
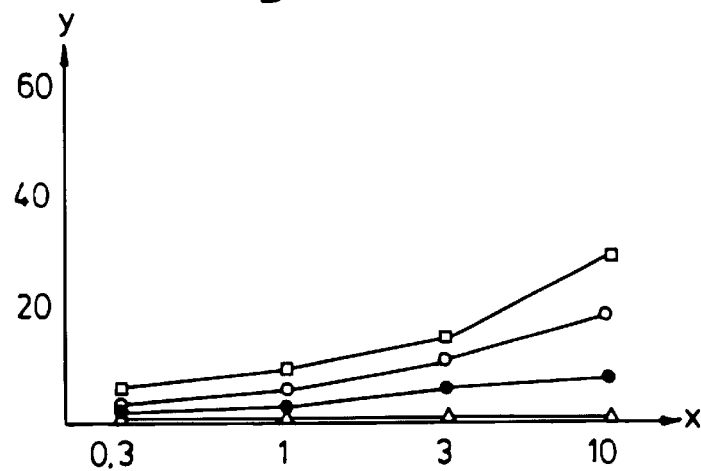

Proliferative responses were also monitored in mice immunised for CTL generation. The protocol was as described above. Spleen cells were taken 3 weeks after the secondary boost. The ability to prime for a proliferative response correlated well with the ability to induce the CTL response. Alhydrogel was substantially less effective than NAGO, FCA or saponin. The data are shown in FIG. 13B. The response to the hybrid (CTL+helper) peptide is shown in A. The response to the helper determinant alone is shown in B, and the response to the CTL determinant alone is shown in C. Clearly, most of the proliferative response is directed at the helper determinant.

EXAMPLE 14
Optimum Dose of the Novel Adjuvant NAGO

Figure 14A:
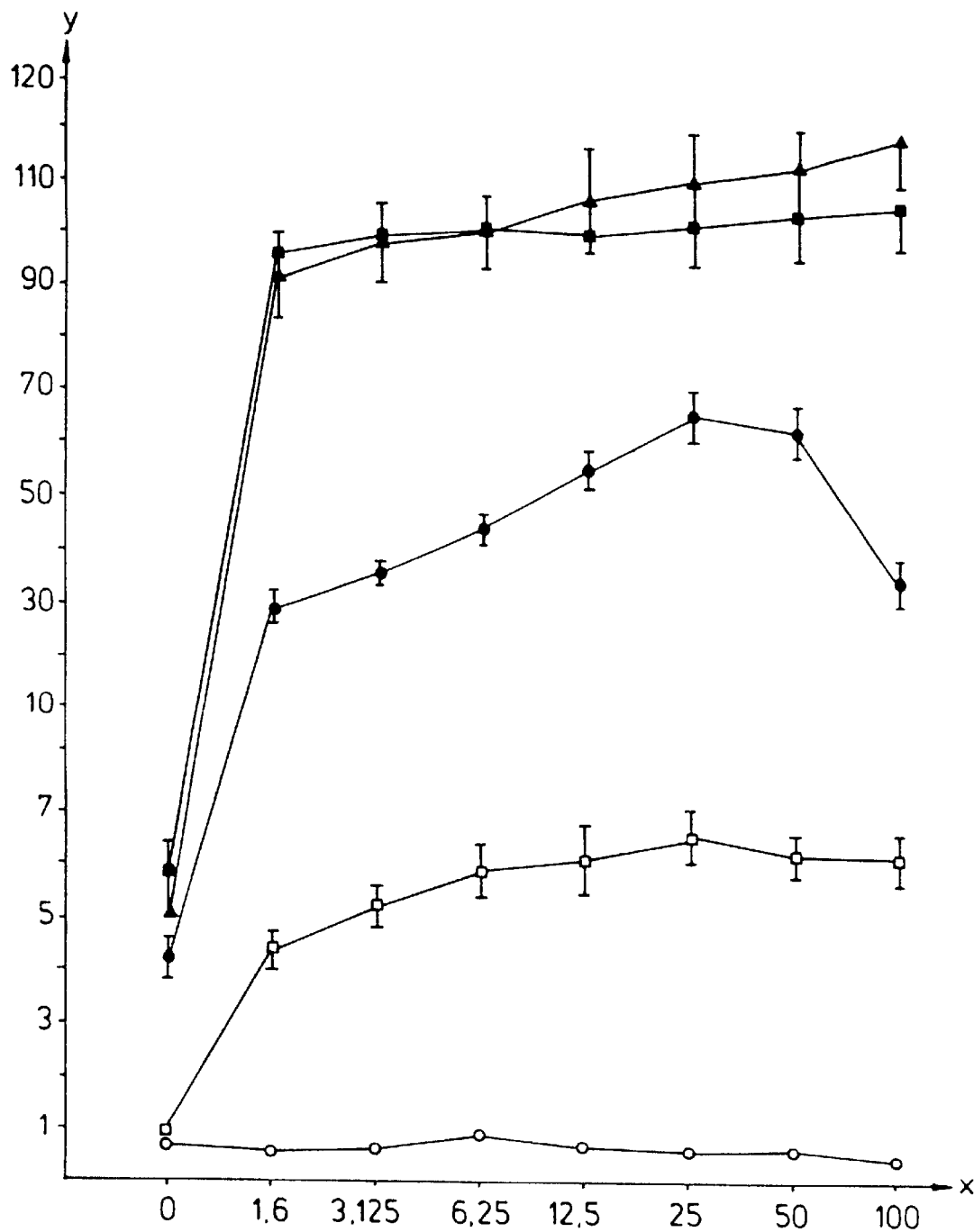
FIG. 14A shows the response of T-cells from mice immunised with a peptide composed of the immunodominant amino acid residues 260 to 283 of the nucleoprotein of influenza A. The concentration of peptide (μg/ml, x axis) is plotted against lymphocyte DNA synthesis ($^3$H-TdR incorporation, cpm×10$^{-3}$ se; y axis) and ■ denotes peptide+NAGO in which the NA is from *Clostridium perfringens*, ▼ denotes peptide+NAGO in which the NA is from *Vibrio cholerae*, • denotes peptide+GO, ☐ denotes peptide alone and ○ denotes no antigen.

The adjuvant effect of GO alone (5 units) with the same dose of GO in combination with 2.5 units of neuraminidase from two different microbial sources: *Clostridium perfringens* and *Vibrio cholerae* was compared. The antigen used was the immunodominant peptide aa260-283 from 'flu NP in B10S mice (1 µg per mouse). T-cell priming was measured by the standard procedure. The results are shown in FIG. 14A. GO alone produced a good adjuvant effect but the combination NA+GO was substantially superior. Neuraminidases from the two different microbial sources were equally effective.

Figure 14B:
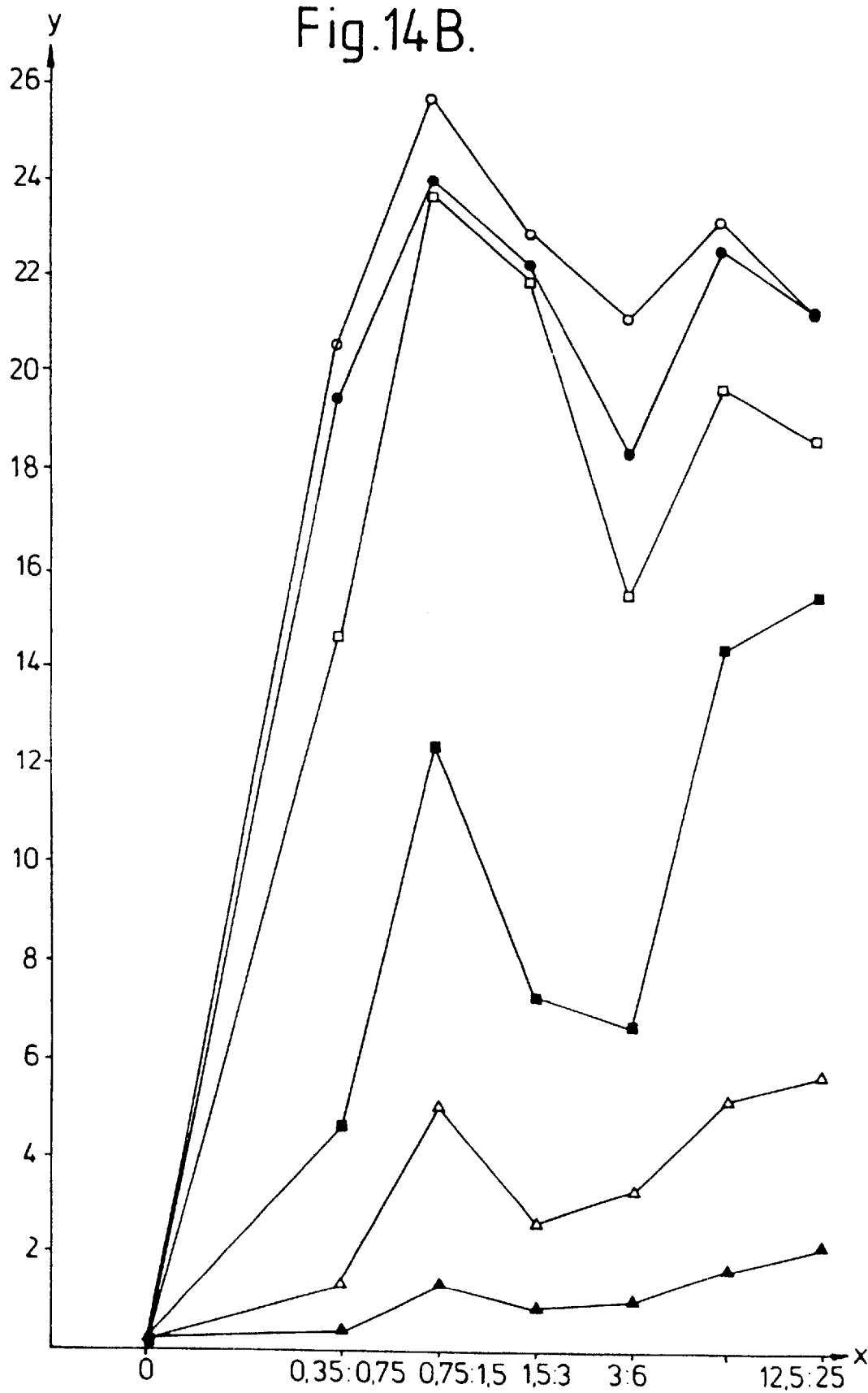
FIG. 14B compares concentrations of NA:GO in units per ml (x axis) which are plotted against lymphocyte DNA synthesis ($^3$H-TdR incorporation, cpm×10$^{-4}$ se; y axis). In the Figure ▼ denotes 0.1 μg of antigen/ml, Δ denotes 0.4 μg of antigen/ml, ■ denotes 1.6 μg of antigen/ml, ☐ denotes 6 μg of antigen/ml, • denotes 25 μg of antigen/ml and ○ denotes 100 μg or antigen/ml.
Figure 14C:
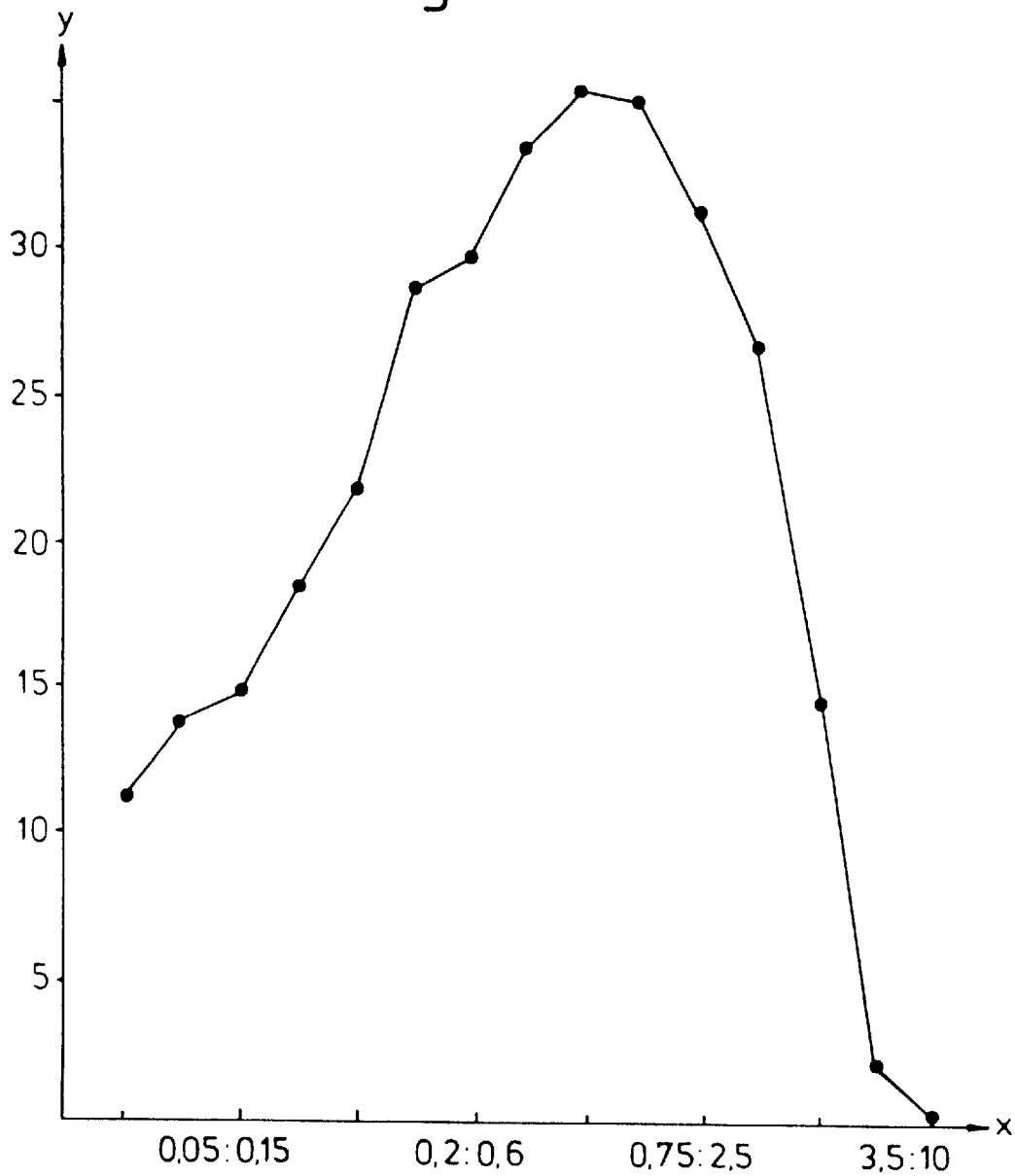
FIG. 14C shows how lymphocyte DNA synthesis ($^3$H-TdR incorporation, cpm×10$^{-4}$ se; y axis) varies with concentration of NA:GO in units/ml (x axis) at a fixed ratio of NA:GO of 1:3.
Figure 14D:
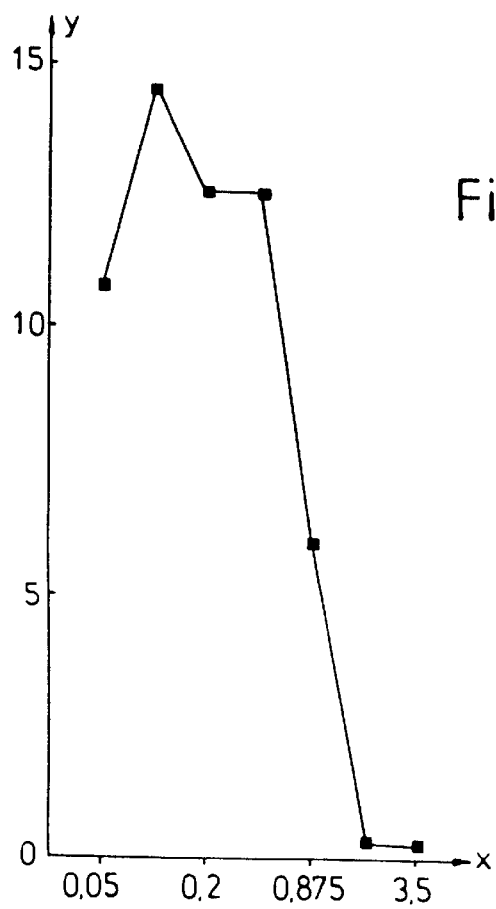
FIGS. 14D and 14E show how lymphocyte DNA synthesis ($^3$H-TdR incorporation, cpm×10$^{-4}$ se, y axis) varies with concentration of NA and GO respectively (units/ml, x axis).
Figure 14E:
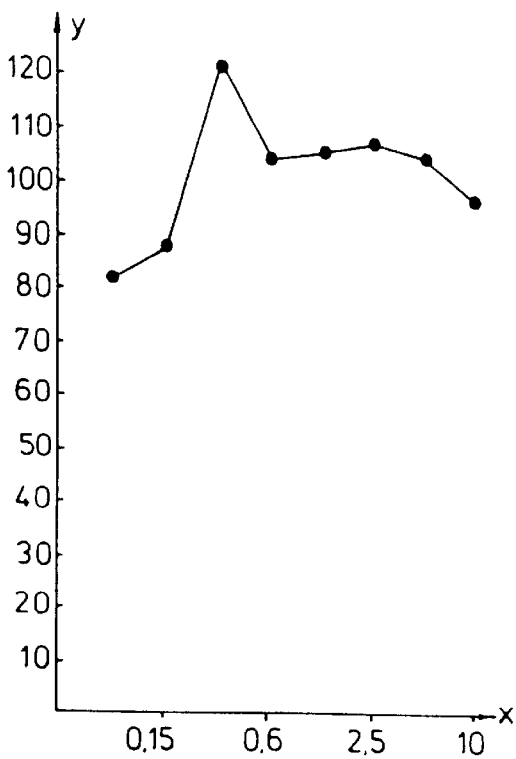

Determination of the optimal dose of NAGO (using NA from Vibrio cholerae) at a fixed ratio of 1:2 neuraminidase:galactose oxidase is shown in FIG. 14B. The concentration of NAGO used in vivo is shown on the x-axis. Each curve is the response to a given concentration of antigen in vitro. A clear optimum was observed at 0.75 units of NA plus 1.5 units of GO. Possible causes of the decreased adjuvant effect seen at higher doses were investigated in vitro and the data are shown in FIGS. 14C–E. The direct (Ag-independent) mitogenic effect of NAGO was assessed by adding NAGO to peripheral blood mononuclear cell (PBMC) cultures. With a fixed ratio of 1:3 NA:GO an optimum was observed above which very marked inhibition was observed (FIG. 14C). Neuraminidase and galactose oxidase were then tested separately for their effects on PBMC proliferation. Some proliferation occurred with NA only but this was steeply limited by increasing dose (FIG. 14D). In contrast, the mitogenic effect of GO was not limited by increasing dose up to 10 units per ml (FIG. 14E). Since it is the neuraminidase and not the galactose oxidase that limits the response with increasing dose, a standard dose of 1 unit NA and 5 units GO was adopted for in vivo use per 100 µl.

EXAMPLE 15
Non-reactogenic Nature of NAGO

No macroscopic lesions were ever observed with NAGO administered subcutaneously in mice. In order to assess the microscopic effects of subcutaneous NAGO administration a comparative histological study of NAGO and alhydrogel was undertaken. Female mice, 8 weeks old were used. One group (6 mice) received the standard dose of alhydrogel (100 µg) subcutaneously and a second group received the standard dose of NAGO (1 unit neuraminidase plus 5 units galactose oxidase) subcutaneously. The test was duplicated in two strains of mice: BALB/c and B10S. At 1, 3, and 6 weeks after the injection, 2 mice from each group were sacrificed and the tissue around the injection site was removed and fixed for histological examination. Initially, the skin samples were examined microscopically and lesions present were identified and scored for severity. Following this, a more detailed assessment of the samples was carried out involving quantification of the cells types present in the subcutis of each skin sample and their distribution in percentage terms. With the exception of two mice given NAGO, which showed no reactions, all treated mice showed low-grade reactions at the s.c. injection site varying in severity from minimal to slight. Subcutaneous injection with either adjuvant induced a low grade inflammatory response in the subcutis characterised by cellular infiltration by macrophages, monocytes, eosinophils and neutrophils, along with some fibroblasts and accompanying collagen deposition. There was no apparent difference between the two strains and no clear pattern of differential pathology with increasing time. All the inflammatory responses were very mild but NAGO induced slightly less inflammation than did alhydrogel.

A question related to the reactogenicity of NAGO is the degree of immunogenicity of the enzymes themselves. Bacterial enzymes are one of the most common groups of antigens and are encountered early in the normal environment. Not surprisingly, normal mouse serum was found to contain detectable levels of antibody reacting with galactose oxidase and, to a slightly lesser extent, with neuraminidase. The standard dose of NAGO (given with the malarial Ag rPMMSA) resulted in only a modest increase in antibody levels to galactose oxidase and a barely detectable increase in antibody to neuraminidase. The amounts of enzymes necessary for an optimal adjuvant effect are very low such that only a local effect on cells at the injection site is possible and this is confirmed by the absence of any significant changes in subcutis cellular infiltration seen in the histopathological study. Very high systemic levels of microbial neuraminidase occur in man in the course of certain bacterial infections. Their pathophysiological effects remains unknown.

REFERENCE EXAMPLE 1
Activity Assay for Galactose Oxidase

Unit Definition: One unit will produce a $\Delta A_{425}$ nm of 1.0 per minute at pH 6.0 at 25° C., in a peroxidase and o-tolidine system. Reaction volume=3.4 ml, 1 cm light path.

Activity Assay

I. Reagents

A. 0.1M Potassium Phosphate Buffer, pH 6.0 at 25° C. (Prepare by mixing 0.1 M $KH_2PO_4$ and 0.1 M $K_2HPO_4$ solutions to obtain a final pH of 6.0).

B. 0.5 (w/v) o-Tolidine Solution (Dissolve 50 mg of o-Tolidine, Prod. No. T-3501, in 10 ml of reagent grade methanol. Store at 0–5° C).

C. Dye-Buffer Solution (Add 0.1 ml of Reagent B, o-tolidine, to 12 ml of Reagent A, potassium phosphate buffer, and mix thoroughly).

D. 10% (w/v) Galactose Substrate Solution (Dissolve 1.0 g of D(+) Galactose, Prod. No. G-0750, in approximately 5.0 ml of deionized $H_2O$. Dilute to a final volume of 10 ml with deionized $H_2O$). Allow to stand at room temperature for 2 hours to allow mutarotation.

E. Peroxidase Enzyme Solution. (Immediately before use, prepare solution in deionized $H_2O$ containing approximately 5 purpurogallin units per ml).

F. Galactose Oxidase Enzyme Solution (Immediately before use prepare a solution in cold Reagent A containing approximately 0.5 units per ml).

Where applicable, all concentrations of reagents indicated above are based on the anhydrous molecular weight.

II. Procedure

Pipet into a quartz or silica cuvet (1 cm light path) as follows:

| | |
|---|---|
| Reagent C (dye-buffer) | 1.70 ml |
| Reagent D (galactose) | 1.50 ml |
| Reagent E (Peroxidase) | 1.10 ml | spectrophotometer with air or a cuvet containing deionized $H_2O$ as the reference. Add:

Reagent F (galactose oxidase) 0.10 ml Immediately mix by inversion and record the increase in $A_{425}$ nm. Obtain the $A_{425}$ nm/minute using the maximum linear rate.

III. Calculation $$\text{Units/ml Reagent } F = \frac{\Delta A_{425\text{nm}}/\text{minute}}{\text{ml Reagent } F/\text{Rxn. Mix}}$$

REFERENCE EXAMPLE 2

Units of Neuraminidase Activity

One unit of neuraminidase activity is equivalent to that amount of enzyme which in 15 minutes at 37° C. will liberate 1 µg N-acetylneuraminic acid from a glycoprotein substrate obtained from human serum (fraction 1, Dische) (N-acetylneuraminic acid is determined by the method of Schuitze et al, Biochem. 1958 239, 490).

What is claimed is:

1. A vaccine formulation comprising an antigenic component and, as an adjuvant component, neuraminidase and galactose oxidase.

2. A formulation according to claim 1, in which the neuraminidase is derived from *Vibrio cholerae* or *Clostridium perfringens*.

3. A formulation according to claim 1 or 2, in which the galactose oxidase is derived from *Dactylium dendroides*.

4. A formulation according to claim 1, in which the ratio of neuraminidase to galactose oxidase in terms of units of activity is from 1:2 to 1:10.

5. A formulation according to claim 1, which contains neuraminidase and galactose oxidase in amount of from 0.2 to 1.2 units of activity and from 2 to 8 units of activity respectively per 100 µl of the said formulation.

6. A formulation according to claim 1, which include a peptide, protein or carbohydrate antigen.

7. A formulation according to claim 1, in which the antigenic component is a bacterial, fungal, protozoal or viral antigen.

8. A formulation according to claim 1, which is a heat killed or attenuated whole organism vaccine.

9. A method of inducing immunity in a patient comprising administering to said patient said vaccine formulation according to claim 1 in an amount sufficient to induce said immunity.

10. A vaccine adjuvant comprising neuraminidase and galactose oxidase.

* * * * *